US012064769B2

(12) United States Patent
Cleveland et al.

(10) Patent No.: US 12,064,769 B2
(45) Date of Patent: Aug. 20, 2024

(54) METHOD FOR CONDUCTING UNIFORM REACTIONS

(71) Applicant: SomaLogic Operating Co., Inc., Boulder, CO (US)

(72) Inventors: Jason Paul Cleveland, Boulder, CO (US); Jon Monserud, Golden, CO (US); Barry Patrick John Vant-Hull, Boulder, CO (US); Alex Kislukhin, Boulder, CO (US)

(73) Assignee: SomaLogic Operating Co., Inc., Boulder, CO (US)

( * ) Notice: Subject to any disclaimer, the term of this patent is extended or adjusted under 35 U.S.C. 154(b) by 0 days.

(21) Appl. No.: 18/087,438

(22) Filed: Dec. 22, 2022

(65) Prior Publication Data

US 2023/0191414 A1 Jun. 22, 2023

Related U.S. Application Data

(60) Provisional application No. 63/292,985, filed on Dec. 22, 2021.

(51) Int. Cl.
*B01L 3/00* (2006.01)
*B01L 7/00* (2006.01)
*B01L 9/00* (2006.01)

(52) U.S. Cl.
CPC .......... *B01L 3/50851* (2013.01); *B01L 7/52* (2013.01); *B01L 9/523* (2013.01);
(Continued)

(58) Field of Classification Search
CPC ........ B01L 3/50851; B01L 7/52; B01L 9/523; B01L 2300/0663; B01L 2300/0829;
(Continued)

(56) References Cited

U.S. PATENT DOCUMENTS 5,925,517 A 7/1999 Tyagi et al.
6,361,486 B1 3/2002 Gordon
(Continued)

FOREIGN PATENT DOCUMENTS

CN 103992945 B 9/2015
CN 112505042 A 3/2021
(Continued)

OTHER PUBLICATIONS

Tyagi, Sanjay et al. "Multicolor Molecular Beacons for Allele Discrimination", Nature Biotechnology, Jan. 1998, vol. 16, Nature Publishing Group http://www.nature.com/naturebiotechnology.
(Continued)

*Primary Examiner* — Jill A Warden
*Assistant Examiner* — John McGuirk
(74) *Attorney, Agent, or Firm* — Kolitch Romano Dascenzo Gates LLC

(57) ABSTRACT

Systems and methods for conducting surface-mediated chemical and/or biochemical reactions within an enclosed chamber are disclosed. Systems and methods of the present disclosure may be used in conducting hybridization reactions of biopolymers. In some examples, an improved method for mixing thin films of solutions in a hybridization chamber includes altering the direction of mixing at least once over the course of a reaction. In some examples, an improved method for mixing thin films of solutions in a hybridization chamber includes altering the speed of mixing at least once over the course of a reaction. In some examples, an improved method for mixing thin films of solutions in a hybridization chamber includes altering the speed of mixing and the direction of mixing at least once over the course of a reaction.

19 Claims, 16 Drawing Sheets

(52) U.S. Cl.
CPC .................. *B01L 2300/0663* (2013.01); *B01L 2300/0829* (2013.01); *B01L 2300/18* (2013.01); *B01L 2400/0403* (2013.01)

(58) Field of Classification Search
CPC ......... B01L 2300/18; B01L 2400/0403; B01L 2300/0819; B01L 2300/0822; B01L 2300/1827; B01L 2400/0409; C12M 23/48

See application file for complete search history.

(56) References Cited

U.S. PATENT DOCUMENTS

| | | |
|---|---|---|
| 6,881,579 B2 | 4/2005 | Hilson et al. |
| 7,205,045 B2 | 4/2007 | Holcomb et al. |
| 7,351,379 B2 | 4/2008 | Schleifer |
| 7,364,896 B2 | 4/2008 | Schembri |
| 7,371,348 B2 | 5/2008 | Schleifer et al. |
| 7,390,457 B2 | 6/2008 | Schembri |
| 7,618,777 B2 | 11/2009 | Myerson et al. |
| 7,807,354 B2 | 10/2010 | Myerson et al. |
| 7,919,308 B2 | 4/2011 | Schleifer |
| 2009/0004681 A1* | 1/2009 | Hoshiko ............ G01N 33/4905 435/13 |
| 2016/0263579 A1 | 9/2016 | Corbett et al. |
| 2018/0361382 A1* | 12/2018 | Zobi .................... B01L 3/50273 |
| 2020/0070145 A1* | 3/2020 | Miura ............... B01L 3/502784 |

FOREIGN PATENT DOCUMENTS

| | | | |
|---|---|---|---|
| JP | 62289174 A | 12/1987 | |
| WO | WO-2009108501 A2 * | 9/2009 | .......... B01F 11/0082 |
| WO | 2019246289 A1 | 12/2019 | |

OTHER PUBLICATIONS

Gold, Larry et al. "Aptamer-Based Multiplexed Proteomic Technology for Biomarker Discovery", PLoS One, Dec. 2010, vol. 5, Issue 12, www.plosone.org.

International Search Report and Written Opinion of the International Searching Authority from the European Patent Office, in PCT/2022/053858 dated May 30, 2023, which is an international application having a common benefit claim with this application.

* cited by examiner

METHOD FOR CONDUCTING UNIFORM REACTIONS

CROSS-REFERENCES

The following applications and materials are incorporated herein, in their entireties, for all purposes: U.S. Provisional Patent Application Ser. No. 63/292,985, filed Dec. 22, 2021.

FIELD

The present disclosure generally relates to an apparatus and methods for improving the uniformity of surface-mediated chemical and biochemical reactions. More particularly, the present disclosure relates to improving the accuracy of microarray technology, such as microarray gene expression profiling, single nucleotide polymorphism (SNP) analysis and/or any assay involving hybridization. Aspects of the present disclosure have utility in fields relating to chemistry, biochemistry, and biology.

INTRODUCTION

Reactions between surface-bound molecules and cognate molecules in solution may be used to enhance reactions. These surface-bound molecules may be selected as probes to detect the presence of target molecules in solution. The surface-bound probes may be oligonucleotides, peptides, polypeptides, proteins, antibodies or other molecules capable of reacting with target molecules in solution. Such reactions are currently used to detect the presence of nucleic acid regions known or suspected to be associated with the natural functioning of a living organism or nucleic acid residues obtained from various sources. Nucleic acids can also be adapted to target molecules through processes such as SELEX (an acronym for Systematic Evolution of Ligands by EXponential enrichment). Many methods of diagnosis of an organism's disease state, metabolic state or life stage rely on the detection of nucleotides. These techniques generally involve hybridization between nucleotides of a target sequence and a complementary probe.

Microarrays are the typical method for quantifying molecules using surface-bound probes. Nucleic acid microarray methods involve hybridization with probe nucleotide sequences immobilized on a substrate and organized in an array typically on the order of square millimeters in area. The array is comprised of heterogeneous features, each feature including a collection of identical probe nucleotide sequences, with typically millions of probe molecules per feature. The substrate comprises a stationary phase and may take the form of beads, colloids, microscope slides, and/or other suitable materials. The substrates may be made of plastic, fused silica, glass, silicon, or other materials. The fluid containing the target molecules comprises the mobile phase. The fluid is contacted with the stationary phase and sealed using a cover slip, gasket, or other suitable means of containing fluids to contact the reaction area. Normally, the reactant targets in the mobile phase diffuse through the liquid to the interface where the cognate probes are immobilized, and a reaction, such as a hybridization reaction, then occurs. In order to monitor the rate of reaction or detect presence of molecules it is preferred that the target molecules in the mobile phase be labeled with a detectable tag. These tags may be fluorescent, magnetic, chemiluminescent, radioactive, or a combination of tags. When a tag is employed, the location of the signal in an array can be used to identify target molecules.

Reactions like and including the hybridization reaction described above typically take place over a time period up to many hours or days. In the chemical and biochemical microarrays, the binding agents are immobilized in a pattern. The patterns from these reactions are typically read by optical means using tagged target molecules that emit light at specific frequencies. Traditionally, the reaction patterns are digitally scanned and analyzed through computational means. These patterns can be used to generate data for disease state detection, identification of drug targets, protein quantification, and the like.

Accurate analysis of the pattern of binding is critical to the efficacy of microarrays. By controlling the reaction environment and conditions the reproducibility and reliability of these patterns can be improved. Merely placing a slide over the reactive substrate results in significant array non-uniformity as well as myriad technical issues, i.e. fluid loss through evaporation. Many constructs have been developed wherein the reactive substrate is mated to a gasket and secured through a variety of means. While mitigating the technical issues of fluid evaporation, the solutions create a system wherein a low volume of fluid is contacted with a reactive substrate in a confined environment.

Conventional mixing methodologies are generally inadequate for mixing of thin films because the capillary strength of the confinement often exceeds the force of mixing. In thin films the bulk of the fluid is contacting the walls of the chamber in a "non-slip" condition. Surface interactions dominate in these systems, creating difficulties in uniform mixing. Therefore, traditional mixing devices that move the chamber in a rocking, shaking, or up and down motion are inadequate.

Mono-directional rotational mixing originated as a simple method for mitigating the difficulties in thin-film mixing. These methods involved nutation, rotation on a rotisserie, orbital mixing, or the like. The implementation of these methods involves rotating the reaction chamber in one direction to induce fluid motion. While improving the reaction efficiency, accuracy, and precision, the mono-directional mixing of the solution leads to hybridization artifacts directly related to direction of rotational mixing. The effects of these artifacts can be mitigated through mathematical means (e.g., processing of the experimental data), however the reaction nonuniformity creates a limitation to microarray patterning in that chemical signaling channels require excessive replicates for robust reactions to compensate for the nonuniformity.

Accordingly, there is a need in the art for an improved device and method for conducting chemical or biochemical reactions on a solid substrate within a thin enclosed chamber, wherein mixing of components is facilitated despite the small volume of the chamber, and further wherein the occurrence of high degrees of reaction uniformity is achieved.

SUMMARY

The present disclosure provides systems, apparatuses, and methods relating to improving reaction uniformity.

In some embodiments, a system for facilitating reactions with improved uniformity comprises: a controller configured to control a motor to impart rotational motion to a rotatable rack for a period of time, wherein the rotatable rack is disposed within a reaction oven and is configured to hold at least one reaction chamber, the reaction chamber containing a functionalized surface and a fluid; wherein the controller is configured to control the motor to change a characteristic of the rotational motion at least once during the period of time.

In some embodiments, a method for mixing a reaction chamber attached to a rotatable rack comprises: automatically controlling a motor coupled to the rack to rotate the rack for a first time interval such that the rotation of the rack has a characteristic having a first value; and automatically controlling the motor to rotate the rack for a second time interval such that the characteristic of the rotation has a second value different from the first value.

In some embodiments, a hybridization oven comprises: one or more walls defining an oven interior; a rack disposed within the oven interior and configured to hold a vessel including one or more reaction chambers; a drive motor configured to rotate the rack about a rotation axis; and an electronic controller configured to automatically control the drive motor to rotate the rack for a duration of time and to automatically adjust a characteristic of the rotation of the rack at least once during the duration.

Features, functions, and advantages may be achieved independently in various embodiments of the present disclosure, or may be combined in yet other embodiments, further details of which can be seen with reference to the following description and drawings.

DETAILED DESCRIPTION

Figure 1:
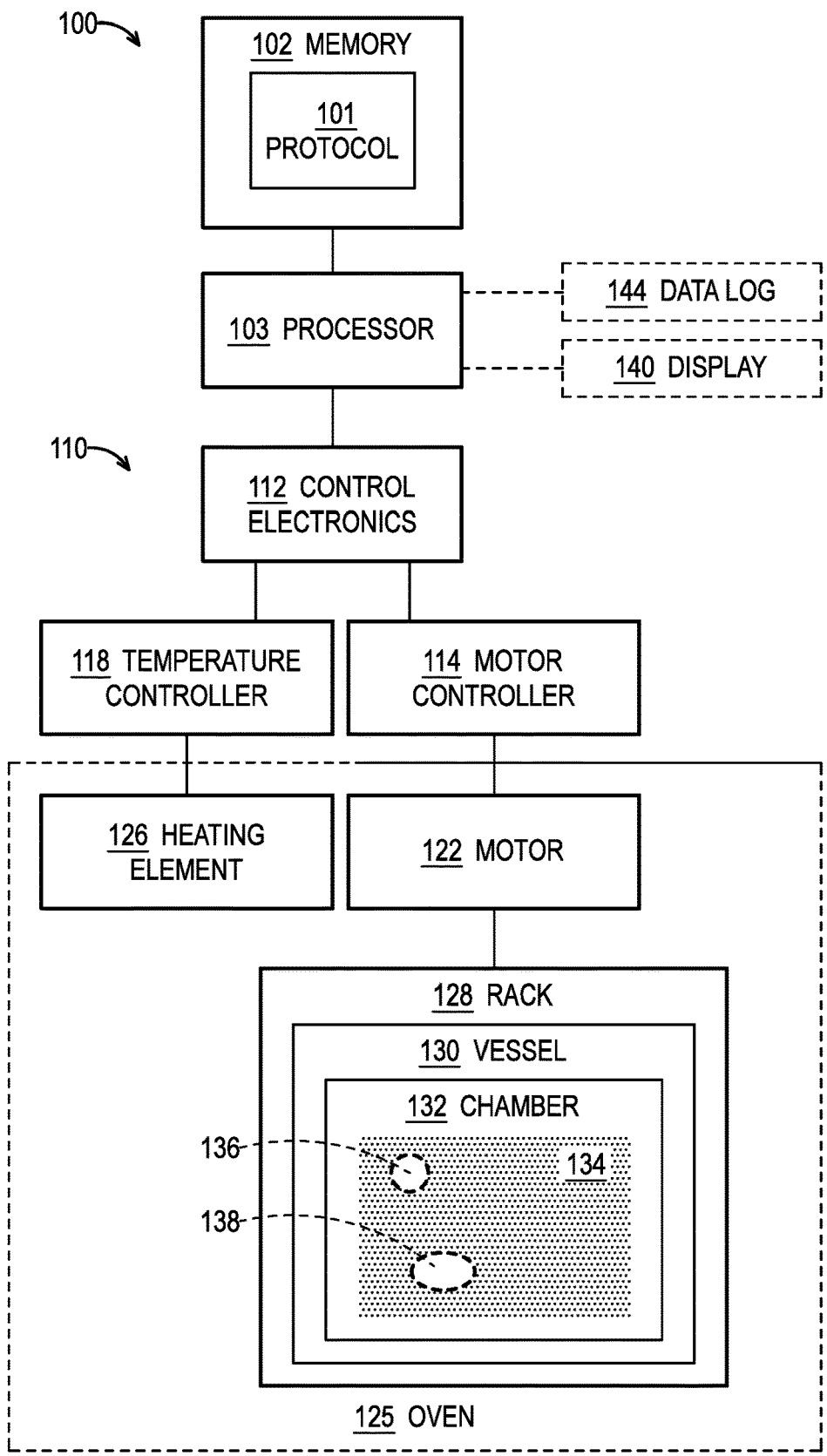
FIG. 1 is a schematic diagram of an illustrative system for conducting reactions with increased uniformity, in accordance with aspects of the present teachings.

Various aspects and examples of systems and methods for facilitating improved reaction uniformity in a reaction chamber are described below and illustrated in the associated drawings. Unless otherwise specified, a reaction system in accordance with the present teachings, and/or its various components, may contain at least one of the structures, components, functionalities, and/or variations described, illustrated, and/or incorporated herein. Furthermore, unless specifically excluded, the process steps, structures, components, functionalities, and/or variations described, illustrated, and/or incorporated herein in connection with the present teachings may be included in other similar devices and methods, including being interchangeable between disclosed embodiments. The following description of various examples is merely illustrative in nature and is in no way intended to limit the disclosure, its application, or uses. Additionally, the advantages provided by the examples and embodiments described below are illustrative in nature and not all examples and embodiments provide the same advantages or the same degree of advantages.

This Detailed Description includes the following sections, which follow immediately below: Definitions; Overview; Examples, Components, and Alternatives; and Conclusion. The Examples, Components, and Alternatives section is further divided into subsections, each of which is labeled accordingly.

Definitions

The following definitions apply herein, unless otherwise indicated.

"Comprising," "including," and "having" (and conjugations thereof) are used interchangeably to mean including but not necessarily limited to, and are open-ended terms not intended to exclude additional, unrecited elements or method steps.

Terms such as "first", "second", and "third" are used to distinguish or identify various members of a group, or the like, and are not intended to show serial or numerical limitation.

Illustrative compositions, reagents, process steps, and/or equipment are described herein as non-limiting examples and are not to be considered in a limiting sense. It is also to be understood that terminology used herein is for the purpose of describing particular examples and is not intended to be limiting.

As used in this specification and the appended claims, the singular forms "a," "an" and "the" include plural referents unless the context clearly dictates otherwise. Thus, reference to "a molecule" includes more than one molecule as well as only a single molecule, reference to "a reactant" includes references to two or more reactants, and so on.

"AKA" means "also known as," and may be used to indicate an alternative or corresponding term for a given element or elements.

The terms "mix" and "mixing" as used herein mean to cause fluids to flow and/or otherwise move within a volume so as to distribute solution components (e.g., across a surface) in a manner that results in more uniform distribution of the solution components than would likely occur without the movement.

The term "substrate" as used herein means a surface upon which molecules may be adhered.

The term "probe" as used herein means a molecule of known identity.

The term "target molecule" refers to a known or unknown molecule in a sample, which is the cognate to a molecular probe.

The terms "array" and "microarray" are used interchangeably herein to refer to an ordered pattern of features adherent to a substrate arranged in a spatially defined and physically addressable manner. Such features may comprise oligonucleotides, peptides, polypeptides, proteins, antibodies, and/or other molecules used to detect sample molecules in a sample fluid.

The term "feature" refers to a single component of an array or microarray comprising identical molecules of oligonucleotides, peptides, polypeptides, proteins, antibodies, and/or other molecules used to detect sample molecules in a sample fluid. A feature may comprise one to many millions of identical molecules.

"Elongate" or "elongated" refers to an object or aperture that has a length greater than its own width, although the width need not be uniform. For example, an elongate slot may be elliptical or stadium-shaped, and an elongate candlestick may have a height greater than its tapering diameter. As a negative example, a circular aperture would not be considered an elongate aperture.

"Coupled" means connected, either permanently or releasably, whether directly or indirectly through intervening components.

"Resilient" describes a material or structure configured to respond to normal operating loads (e.g., when compressed) by deforming elastically and returning to an original shape or position when unloaded.

"Rigid" describes a material or structure configured to be stiff, non-deformable, or substantially lacking in flexibility under normal operating conditions.

"Elastic" describes a material or structure configured to spontaneously resume its former shape after being stretched or expanded.

"Processing logic" describes any suitable device(s) or hardware configured to process data by performing one or more logical and/or arithmetic operations (e.g., executing coded instructions). For example, processing logic may include one or more processors (e.g., central processing units (CPUs) and/or graphics processing units (GPUs)), microprocessors, clusters of processing cores, FPGAs (field-programmable gate arrays), artificial intelligence (AI) accelerators, digital signal processors (DSPs), and/or any other suitable combination of logic hardware.

A "controller" or "electronic controller" includes processing logic programmed with instructions to carry out a controlling function with respect to a control element. For example, an electronic controller may be configured to receive an input signal, compare the input signal to a selected control value or setpoint value, and determine an output signal to a control element (e.g., a motor or actuator) to provide corrective action based on the comparison. In another example, an electronic controller may be configured to interface between a host device (e.g., a desktop computer, a mainframe, etc.) and a peripheral device (e.g., a memory device, an input/output device, etc.) to control and/or monitor input and output signals to and from the peripheral device.

Directional terms such as "up," "down," "vertical," "horizontal," and the like should be understood in the context of the particular object in question. For example, an object may be oriented around defined X, Y, and Z axes. In those examples, the X-Y plane will define horizontal, with up being defined as the positive Z direction and down being defined as the negative Z direction.

"Providing," in the context of a method, may include receiving, obtaining, purchasing, manufacturing, generating, processing, preprocessing, and/or the like, such that the object or material provided is in a state and configuration for other steps to be carried out.

In this disclosure, one or more publications, patents, and/or patent applications may be incorporated by reference. However, such material is only incorporated to the extent that no conflict exists between the incorporated material and the statements and drawings set forth herein. In the event of any such conflict, including any conflict in terminology, the present disclosure is controlling.

Overview

In general, the present disclosure describes systems and methods for conducting chemical and biochemical reactions involving mixing. Generally, the uniformity of reactions facilitated by aspects of the present teachings is significantly improved compared to the uniformity achieved in conventional systems.

In some examples, the reactions involve a solid surface disposed within an enclosed reaction chamber, and mixing of components within the chamber is facilitated by rotation of the chamber. Illustrative examples of this type are discussed below and generally throughout the application. However, in general, systems and methods for mixing in accordance with aspects of the present teachings are suitable for facilitating any reaction (or other suitable process and/or phenomenon) involving mixing. Systems and methods configured for automatic adjustment of a direction and/or speed of mixing (e.g., direction and/or speed of rotation about one or more axes) associated with any suitable reaction is within the scope of the present disclosure.

In some examples, reaction uniformity and/or kinetics between, e.g., surface-bound molecules and cognate molecules in solution are improved by changing the direction of mixing, rotation, and/or nutation at least once during a reaction and/or by varying the speed of mixing, rotation, or nutation at least once over the course of a reaction. A reaction chamber or other suitable object may be rotated about any suitable number of rotation axes. In some examples, the object is rotated about a single axis. In some examples, the object is rotated about two or more axes, which may be orthogonal or nonorthogonal. The speed and/or direction of rotation may be varied, in accordance with aspects of the present teachings, with respect to all axes and/or any suitable subset of axes, including just one axis, in any suitable manner. Changes in speed and/or direction of rotation about any given axis may be independent of the rotation about any other axis or may be related to the rotation about other any other axis or axes in any suitable manner.

In some examples, an apparatus for facilitating reactions includes a substrate with a reaction area on which the chemical or biochemical reactions are conducted, wherein the reaction area comprises a portion of the substrate or comprises another substrate disposed on or adjacent the original substrate, and a cover wherein the cover and the substrate form an enclosure having an interior space that serves as the reaction chamber. The chamber is designed to retain a quantity of fluid so that the fluid is in contact with an inner surface of the substrate including the reaction area. As a result of this arrangement, the fluid may also contact the inner surface of the cover.

The cover may be made of glass, plastic, fused silica, silicon, and/or any other suitable material(s). Suitable materials for the cover may include materials that are thermally stable, chemically inert, and rigid, and/or any other suitable material(s).

Additionally, in some examples the cover has a raised portion around the portion of the cover comprising the reaction chamber. The raised portion may be constructed by machining, molding, dispensing, and/or any other suitable technologies. As noted above, the cover and substrate combine to form the reaction chamber. The raised perimeter of the reaction chamber forms a tight seal between cover and substrate. Pressure is applied to the construct by clamps, rigid framing, a press, and/or any other suitable device(s) in order to maintain the sealed reaction chamber.

The reaction chamber assembly described above is secured into a rack and/or other suitable apparatus by straps, clips, magnets, and/or any other suitable means of securing the construct, so that the chamber may be moved by mechanical, manual, and/or other means. The fluid or fluids therein moves and results in mixing between the fluid and the molecules attached to the reaction area. This idea may be incorporated in contexts wherein chemical or biochemical reactions are to be conducted on a substrate surface in an enclosed chamber. It will be understood that the reaction chamber construct of substrate, cover, means of securing, means of manipulation, or other components may take any suitable form, not limited to the illustrative examples described herein. In some examples, the rack (or other apparatus configured to hold a reaction chamber and/or reaction chamber assembly) is disposed within a reaction oven (e.g., a hybridization oven).

A method of moving the reaction chamber in accordance with aspects of the present teachings incorporates at least one change of direction and/or rotational speed of the reaction chamber during a reaction period (e.g., during a time period in which the reaction chamber is subjected to conditions intended to facilitate reaction(s), which may be, e.g., the time period for which the reaction chamber is disposed in the reaction oven). In some examples, changing the direction or speed of rotation of the chamber is accomplished by changing the direction or speed of rotation of a rotatable rack securely holding the chamber.

In some examples, digital controls are added to an oven already having manual inputs for manipulation of environment and chamber movement (e.g., manual oven controls), such that the oven is automatically controllable by the digital controls. The manual controls are supplemented and/or replaced by digital controls (e.g., processing logic) configured to automatically rotate the rack according to a program including at least one change of direction and/or at least one change in rotational speed, and optionally to automatically control temperature and/or other environmental parameters. Digital control allows for continuous automatic control over reaction chamber movement and/or environment. Accordingly, an apparatus incorporating digital control is configured to automatically change a direction of reaction chamber movement, a speed of reaction chamber movement, a rate of change of reaction speed and/or direction, one or more environmental parameters, any other suitable parameter, and/or any combination of the aforementioned parameters over the course of a reaction period.

A set of instructions for controlling motion of a reaction chamber within an oven and/or environmental factors such as a temperature of the oven may be referred to as a Protocol. In some examples, the Protocol lists motor speed of a motor configured to rotate the rack (expressed as, e.g., rpm, a set of discrete levels (e.g., 0-15,) each corresponding to a different rpm, and/or any other suitable expression), direction (e.g., clockwise or counterclockwise relative to a suitable reference), and temperature, for each of one or more time increments (e.g., 1-minute time increments). In some examples, the Protocol includes time increments that are not all equal in duration. In some examples, the Protocol specifies rate(s) of change in temperature and/or rotation speed for each time increment, and/or a rate of change of rotation speed to be used in changing the rotation direction of the rack (e.g., how quickly the rack reverses rotation direction). Protocols used to effect hybridization with greater reaction uniformity, and software and hardware configured to implement these Protocols, are contemplated herein.

In some examples, at least some aspects of a Protocol are determined randomly and/or pseudorandomly (e.g., based on the output of a random number generator). For example, motor speed(s) associated with one or more time increments of the Protocol may be determined at random. As another example, it may be determined at random whether a direction of rotation will change (as opposed to staying constant) at a given time increment of the Protocol. Speed of rotation (e.g., motor speed), direction of rotation, temperature, duration of time increment, and/or any other suitable parameters may be selected at random. Random values may be selected by any suitable method(s) from any suitable distribution(s) (e.g., uniform, normal, etc.). The randomly selected values may be, at least to good approximation, statistically uncorrelated with each other, which tends to result in a high degree of mixing uniformity.

A Protocol can be loaded into a computer-readable memory in a form that can be read by a processor (e.g., by a software program resident in the processor). The processor may be referred to as a central processing unit, AKA a CPU, which may be, e.g., part of a computer or a free-standing microprocessor. An example of a program suitable for reading the Protocol is Igor Pro™, with the Protocol being loaded into memory in the form of an Igor data wave.

The interpretation of the Protocol by the CPU and/or resident program leads to the CPU issuing commands (e.g., at specified time increments) to a control system (e.g., one or more electronic controllers), which in response issues signals (e.g., electric signals) to a motor coupled to the rack, optionally a heating element of an oven in which the rack is disposed, and/or any other suitable device(s). In some examples, the control system comprises a motor controller configured to control the motor, processing logic configured to receive commands from the CPU and to control the motor controller based on the received commands, and optionally a temperature controller configured to control a heating element and to be controlled by the processor based on the received commands. However, in general the control system may comprise any suitable arrangement of processing logic.

In some examples, including examples in which the Protocol is implemented as an Igor data wave, the commands issued by the CPU are text commands sent via USB cable. Alternatively, or additionally, the commands may be electronic signals (e.g., voltage, current, or resistance, pulsed or steady, AC or DC).

In some examples, the control system is configured to receive and execute instructions from the CPU in real time or near-real time. Alternatively, or additionally, the control system may be configured to receive instructions in advance (e.g., to receive instructions for controlling the rack and oven over an entire reaction period before the beginning of the reaction period, and/or any other suitable arrangement). In examples in which one or more parameters of a Protocol are determined randomly, the random values may be determined in advance (e.g., using the CPU), such that the random values are determined before the control system receives instructions (e.g., before the Protocol is converted by the CPU into instruction(s) readable by the control system). For example, all random values of the Protocol may be determined before the Protocol is converted into instructions readable by the control system. In some examples, however, the random values are determined at the CPU and converted into instructions to be executed in real time or near real time (e.g., such that the random value(s) associated with a given time increment are determined at the beginning, or immediately before the beginning, of that time increment). In general, any suitable timing for determining any or all random value(s) of a Protocol may be used.

In some examples in which the instructions are loaded into a memory of the controller in advance, the CPU is not coupled to the controller during the reaction. However, keeping the CPU coupled to the controller during the reaction may facilitate other functions, such as transmitting data from the reaction chamber to the CPU for logging, analysis, and/or presentation to a user.

Examples, Components, and Alternatives

The following sections describe selected aspects of illustrative apparatuses configured to facilitate reactions with high uniformity, as well as related systems and/or methods. The examples in these sections are intended for illustration and should not be interpreted as limiting the scope of the present disclosure. Each section may include one or more distinct embodiments or examples, and/or contextual or related information, function, and/or structure.

A. Illustrative System

With reference to FIGS. 1-5, this section describes an illustrative system 100 for facilitating highly uniform reactions, in accordance with aspects of the present teachings. System 100 is an example of the system described generally in the Overview above.

FIG. 1 is a schematic diagram depicting system 100. A machine-readable Protocol 101 (which may optionally be human-readable as well, e.g., included in a human-readable text file, accessible via a graphical user interface, and/or otherwise readable by a human user) comprises processor-executable instruction(s). Protocol 101 includes instructions identifying a motor speed (which in this example is identified in the Protocol as a numerical level in the range 0-15, each level corresponding to a different motor speed in rpm), motor direction (in this example, clockwise or counterclockwise), and temperature. In this example, a motor speed, a motor direction, and a temperature are specified by the Protocol for each of one or more 1-minute time increments. Other time increments, including time increments of different durations, may alternatively or additionally be used.

Protocol 101 is loaded into a computer-readable memory 102, which is accessible by a central processing unit (CPU) 103. CPU 103 may comprise any suitable processor(s) and may reside in a desktop computer, laptop computer, tablet, microcontroller, and/or any other device suitable for including a central processing unit (e.g., such that the central processing unit is easily physically accessible by data cables and/or other connectors). Memory 102 may reside internal or external to the device that houses CPU 103, and may comprise a hard disk, disk drive, flash drive, tape drive, and/or any other suitable device configured to store and/or allow retrieval of digital information.

CPU 103 interprets instructions of Protocol 101 and sends appropriate commands (e.g., digital commands) to control system 110 based on the Protocol. Control system 110 may include any suitable processing logic for receiving commands from CPU 103 and outputting appropriate signals based on the received commands. In this example, control system 110 includes control electronics 112, a motor controller 114, and a temperature controller 118. Control electronics 112 is configured to receive commands from CPU 103 and to control motor controller 114 and temperature controller 118 based on the received commands to implement Protocol 101. In some examples, control electronics 112 is retrofitted to an apparatus already including the temperature controller and motor controller.

Based on commands from CPU 103, control electronics 112 outputs appropriate signals for motor speed and direction to motor controller 114, and outputs appropriate signals for temperature to temperature controller 118. Control electronics 112 may be configured to output digital or analog electronic, optical, and/or electro-mechanical signals, depending on what is suitable for the controllers.

Motor controller 114 is configured to control a drive motor 122 (e.g., by sending suitable signals to the drive motor, by controlling the power amplitude or power waveforms to the drive motor, and/or in any other suitable manner) and temperature controller 118 is configured to control a heating element 126 (e.g., by sending suitable signals to the heating element, by controlling the amplitude of the power to the heating element, and/or in any other suitable manner). Drive motor 122 and heating element 126 are included in a reaction oven 125. Drive motor 122 is coupled to a rotatable rack 128 disposed within an enclosure of the reaction oven 125. Heating element 126 may be disposed in any suitable location for selectively heating the enclosure. Aspects of control system 110 (e.g., control electronics 112, motor controller 114, and temperature controller 118) may disposed in any suitable location (e.g., within the enclosure, within walls of the oven, attached to an exterior of the oven, spaced from the oven and coupled to it via electrical connectors, etc.). In some examples, at least some portions of control system 110 are integrated into the oven. For example, the motor controller and temperature controller may be integrated into the oven, and control electronics 112 may be coupled to the oven mainly or only by electrical connections to the motor controller and temperature controller. In some examples, the control electronics is configured to control the motor controller and/or temperature controller wirelessly (e.g., without cables or other physical connections between the control electronics and the controllers).

Motor controller 114 is configured to regulate drive power to drive motor 122, which converts the power to rotational motion of rack 128. Drive motor 122 may be an AC motor, DC motor, stepper motor, servomotor, internal combustion engine, and/or any other suitable device that converts power in electrical and/or chemical form into rotational motion.

Rack 128 may take any form suitable for holding one or more reaction vessels 130. Reaction vessel 130 may comprise any device suitable for holding and/or at least partially defining one or more reaction chambers 132. Reaction chamber 132 includes a surface 134 having attached molecules. Chamber 132 is configured to contain a fluid, which is caused to move across at least portions of surface 134 by the movement of rack 128 caused by motor 122. Optionally, one or more bubbles 136 and/or one or more particles 138 may be disposed within chamber 132 (e.g., within fluid disposed within the chamber) to help improve mixing.

Rack 128 is configured to hold reaction vessel 130 such that a normal vector to the reaction area of reaction chamber 132 (e.g., a vector normal to surface 134) is parallel to an axis of rotation of the rack (see FIG. 2 for an illustrative example), or parallel to a vector component of the axis of rotation of the rack. Other configurations that facilitate uniformity of mixing within the reaction chamber may alternatively or additionally be used. One such alternative configuration is centrifugal planetary mixing, in which the reaction vessel rotates about a second axis of rotation in addition to (e.g., at the same time as) rotating about the axis of rotation of the rack. The second axis of rotation is parallel to the axis of rotation of the rack and passes through the center of the reaction vessel (e.g., normal to the reaction surface, and in some cases in the location of vector 170 depicted in FIG. 2). Accordingly, the second axis of rotation itself rotates about the axis of rotation of the rack as the vessel rotates about the rack. In this configuration, the rotation speed of the rack is fast enough to produce circa 100 g of centrifugal acceleration, while the rotation speed of the reaction vessel is circa 10 rpm. This is possible because in at least some examples lacking planetary motion, if the rotation speed of the rack is too fast, then centrifugal force may overwhelm the force of gravity, rendering any bubble in the chamber unable to move around the chamber. For example, in some cases the rack rotation speed should be kept below approximately 60 RPM to avoid immobilizing the bubble. In an example including planetary motion, however, rotation about the second axis results in centrifugal force not always having the same direction relative to the chamber. As a result, the relative timing of rotation about the rack axis and rotation about the second axis can be selected such that the bubble moves about most or all of the chamber without getting stuck or failing to reach certain portions of the chamber. A centrifugal planetary configuration produces a force of gravity that is much greater (e.g., in the range of 10× greater to 50× greater and in some cases as much as 100× or more greater) than in the example of FIG. 2. The greater force corresponds to a greater movement speed of any bubble in the reaction chamber, which tends to help increase mixing.

Heating element 126 may include any suitable device configured to adjust a temperature of oven 125 (e.g., of a chamber of oven 125) in response to signals from temperature controller 118. For example, heating element 126 may include a resistive heating device, and temperature controller 118 may be configured to control the temperature of oven 125 by selectively supplying power to the resistive heating device.

Feedback loops may be optionally included in system 100. For example, in some cases a temperature of a chamber of oven 125 is controlled by a feedback loop, with heating element 126 being configured to maintain a temperature of the chamber at a setpoint temperature commanded by the temperature controller based on Protocol 101. In these cases, heating element 124 includes, and/or is coupled to, a device configured to send heater feedback to temperature controller 118 indicating how much the temperature in reaction oven 125 (e.g., as sensed by a temperature probe configured to sense temperature within the oven chamber) deviates from the desired setpoint. In response to the heater feedback, temperature controller 118 is configured to control heating element 126 to compensate for the deviation.

In some examples, temperature controller 118 is configured to send temperature data (including, e.g., a sensed temperature of the oven chamber, the setpoint temperature, and/or any other suitable temperature data) to control electronics 112, which is configured to transmit the temperature data (and/or a subset of the data, a result of computations performed on the data, and/r the like) to CPU 103. Control electronics 112 may be configured to interpret the received data (e.g., to convert the data into a format readable by CPU 103) prior to transmitting it to CPU 103.

In some examples, drive motor 122 is configured to send drive data to motor controller 114, which is configured to send speed data (including, e.g., a sensed motor speed, and/or any other suitable data) based on the drive data to control electronics 112. Control electronics 112 is configured to send the speed data (and/or a subset of the data, a result of computations performed on the data, and/or the like) to CPU 103. Control electronics 112 may be configured to interpret the received data prior to transmitting it to CPU 103.

In some examples, CPU 103 is configured to display received data (e.g., temperature data, speed data, and/or any other suitable data) on a data display device 140 and/or to log the data on a data logging device 144. Data display device may comprise a monitor, an LED display, an LCD display, and/or any other device suitable for displaying information in a human-perceptible manner. Data logging device 144 may comprise any suitable device for storing information, and in some cases may be a partition of memory 102.

Figure 2:
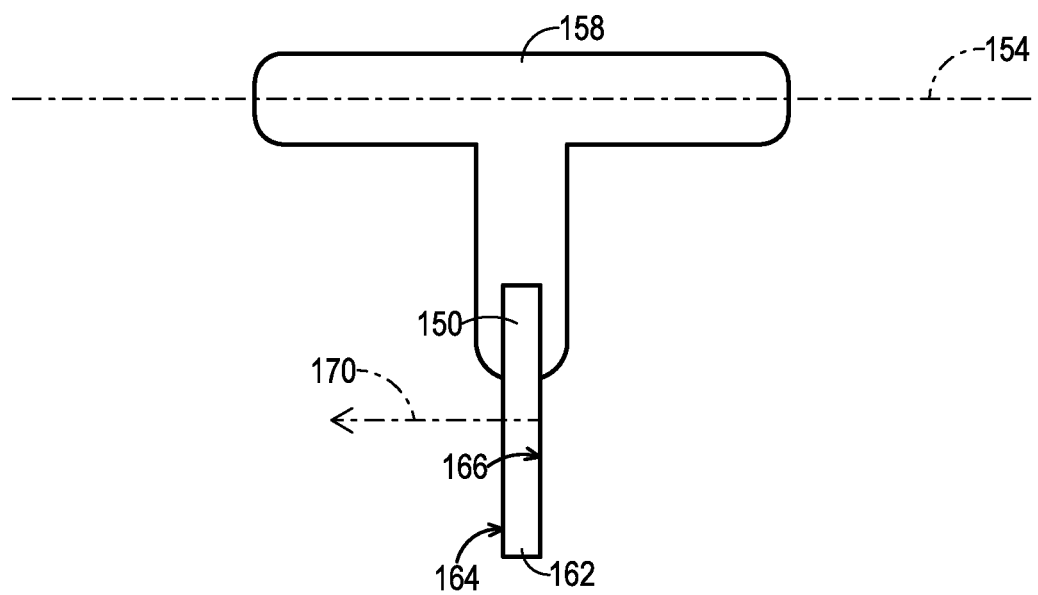
FIG. 2 is a schematic front view of an illustrative rack and reaction chamber of the system of FIG. 1, in accordance with aspects of the present teachings.

FIG. 2 is a schematic diagram depicting an illustrative configuration of a reaction chamber 150 relative to a rotational axis 154 of a rotatable rack 158, in accordance with aspects of the present teachings. Reaction chamber 150 has at least one side wall 162, a front wall 164, and a reaction surface 166. Reaction surface 166 may comprise at least part of a floor of the chamber and/or a ceiling of the chamber, such that the reaction surface is exposed to contents of the chamber (e.g., fluids disposed within the chamber). A plurality of molecules are bound to reaction surface 166. The surface-bound molecules act as probes to detect the presence of target molecules in solution within the reaction chamber. A normal vector 170 is defined normal to reaction surface 166. As shown in FIG. 2, normal vector 170 may be parallel to front wall 164 of reaction chamber 150.

Reaction chamber 150 is mounted on rack 158, which is configured to rotate about rotational axis 154. Rack 158 may have any suitable form configured to securely hold reaction chamber 150 (and/or a device including reaction chamber 150, optionally along with one or more additional reaction chambers) such that normal vector 170 of the reaction chamber is parallel to rotational axis 154 of the rack. Rack 158 holds reaction chamber 150 at a distance from rotational axis 154, such that rotation of the rack causes the reaction chamber to move in a path about the rotational axis. The reaction chamber travels the path about the rotational axis in a direction determined by the direction of rotation of the rack at a speed determined by the rotation speed of the rack. Optionally, to mitigate the effects of centrifugal forces, the reaction chamber may be located at the rotational axis, with the normal vector 170 parallel to rotational axis 154. The direction and speed of rotation of the rack are based on, e.g., a direction and speed of a motor driving the rack.

In other examples, a rack may be configured to hold a reaction chamber at any suitable orientation and/or position relative to a rotational axis of the rack. For example, a normal vector of the reaction chamber may be orthogonal to the rotational axis, orthogonal to and spaced from the rotational axis, coaxial with the rotational axis, and/or oriented in any other suitable manner. In some cases, the rack holds a device containing a plurality of reaction chambers. In cases in which the device has a plurality of reaction chambers, each reaction chamber may be oriented such that a normal vector to a reaction surface of the reaction chamber is parallel to the rotational axis. Alternatively, the reaction chambers may not all have a same orientation relative to the rotational axis (e.g., respective normal vectors defined by the reaction surfaces of the reaction chambers may not all be parallel with each other).

Figure 3:
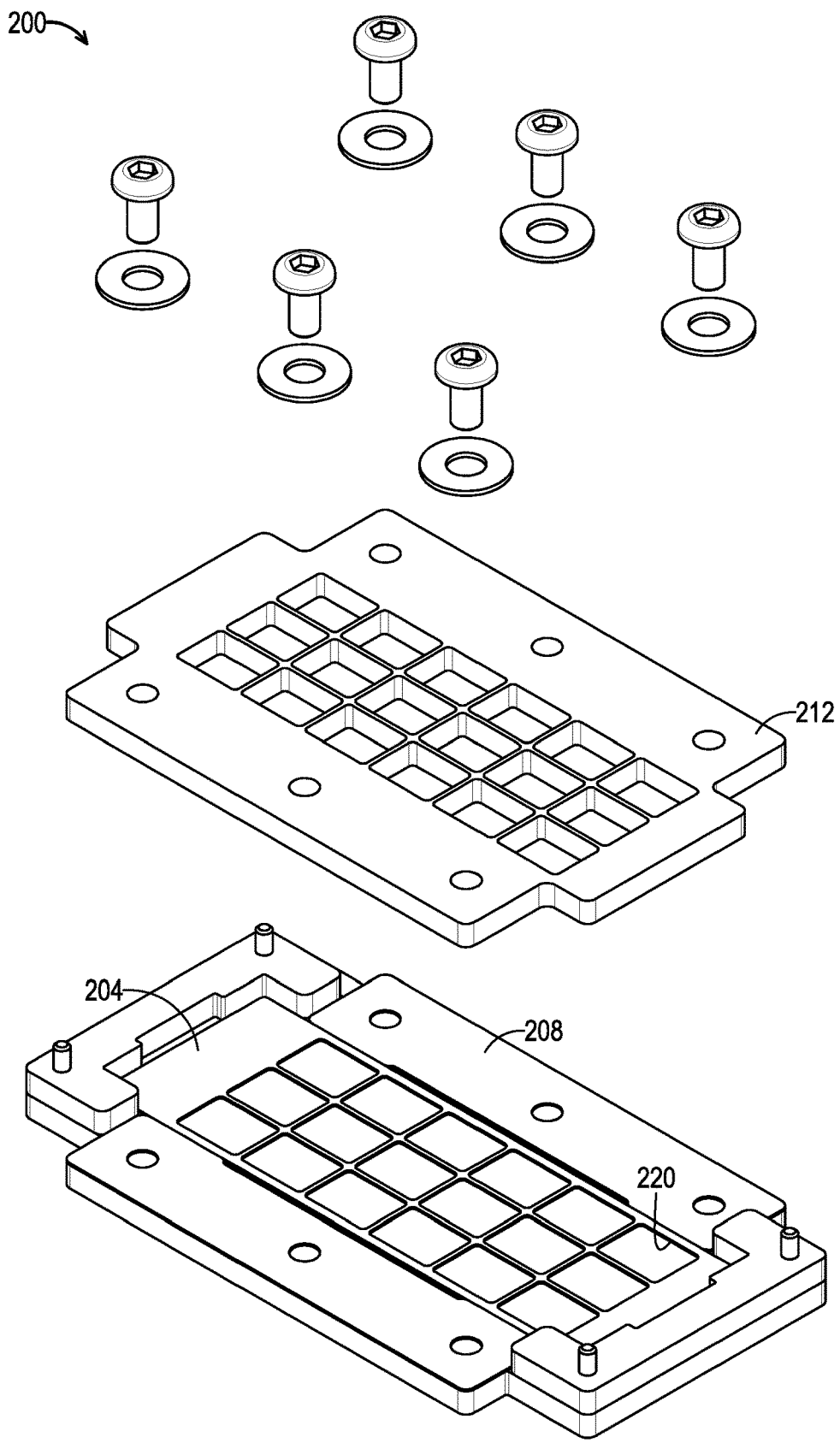
FIG. 3 is an exploded view of an illustrative reaction vessel including reaction chambers, in accordance with aspects of the present teachings.

FIG. 3 is a partially exploded view of an illustrative reaction vessel 200 suitable for holding reaction chambers to be mixed in a reaction system in accordance with aspects of the present teachings. Vessel 200 is an illustrative example. In general, any suitable vessel may be used.

Vessel 200 includes a substrate 204 configured to be disposed between a vessel bottom 208 and a vessel top 212, with vessel bottom 208 supporting substrate 204 (e.g., within a recess formed in the vessel bottom and configured to receive substrate 204, as in the depicted example). In some examples, substrate 204 is a microscope slide.

One or more reaction chambers 220 are defined on substrate 204. In this example, the substrate has eighteen reaction chambers, but any suitable number may be used. At least one interior surface (e.g., a floor or ceiling) of each chamber is functionalized, the functionalized surface(s) being the reaction surface(s) of the reaction chambers. In the depicted example, the vessel top and bottom are configured to be held together by fasteners. In some examples, a clamp is used to clamp the vessel bottom and vessel top together with the substrate between them, which may help to seal the reaction chambers against fluid egress.

Figure 4:
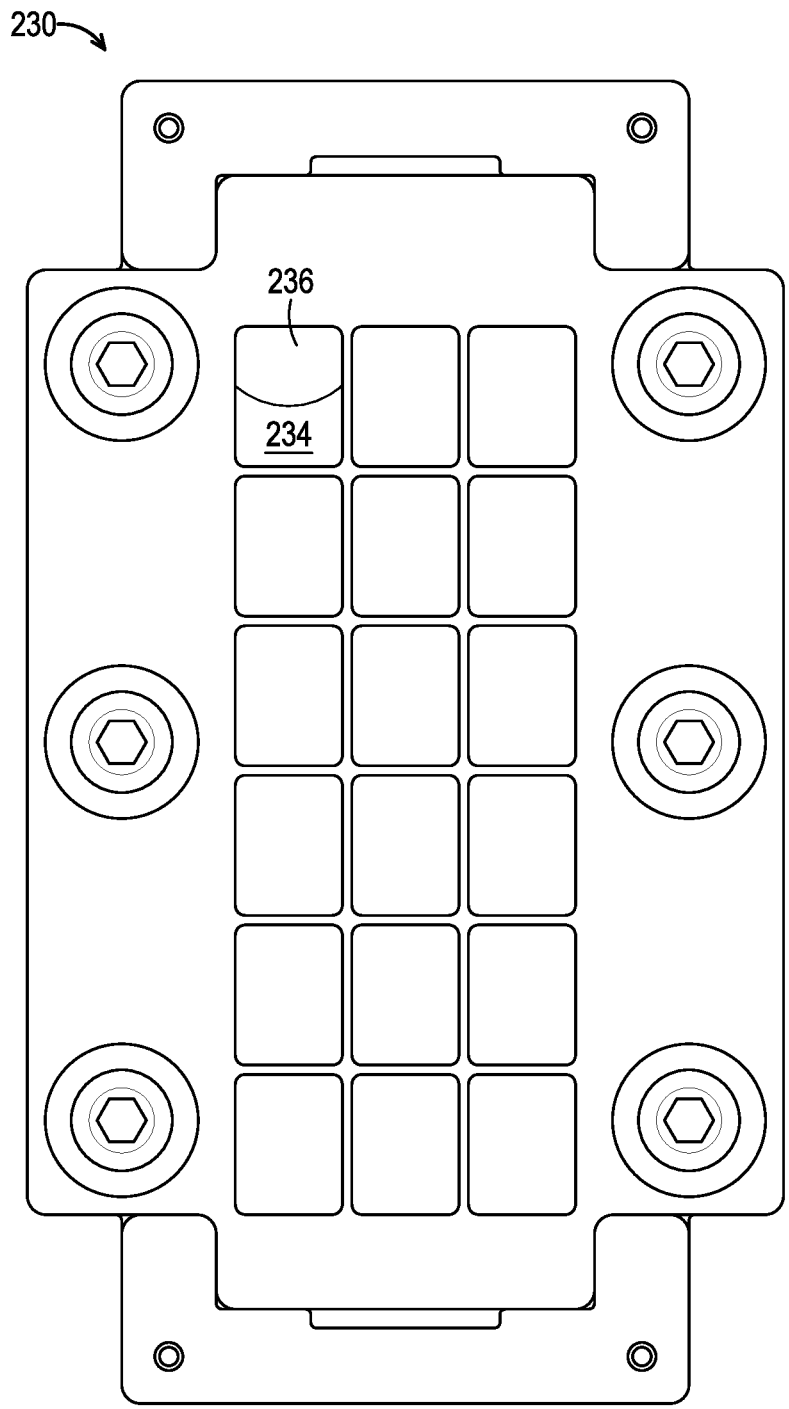
FIG. 4 is a bottom view of another illustrative reaction vessel, in accordance with aspects of the present teachings.

FIG. 4 is a bottom view of another illustrative reaction vessel 230. Windows formed in the vessel allow fluid 234 within a reaction chamber to be seen. A bubble 236 is disposed within the chamber.

Figure 5:
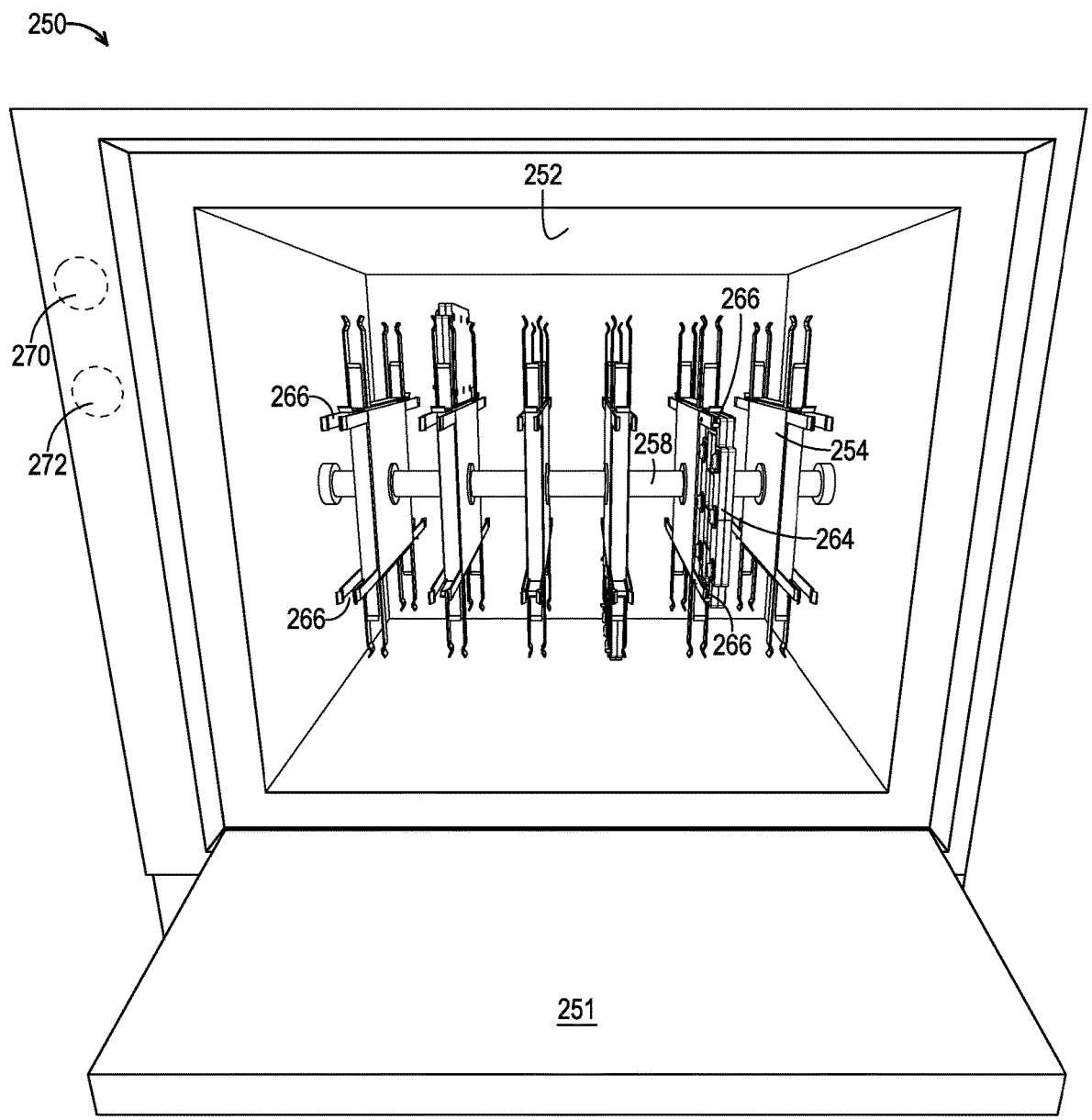
FIG. 5 is a front view of an illustrative hybridization oven in accordance with aspects of the present teachings.

FIG. 5 is a front view of an illustrative automatically controllable reaction oven 250 in accordance with aspects of the present teachings. Oven 250 has one or more walls and a door 251 defining an oven interior 252 (AKA an enclosure). A plurality of racks 254 each rigidly attached to a shaft 258 are disposed within oven interior 252. Shaft 258 is configured to rotate within the enclosure. For example, the shaft may be attached at a first end to a shaft coupling configured to couple the shaft to a drive motor such that the drive motor rotates the shaft and rack(s). The shaft may be supported at a second end by a bushing and/or other suitable device configured to allow the shaft to rotate.

Each rack 254 is configured to securely hold a reaction vessel 264, which is substantially similar to reaction vessel 230 and/or 200. In the depicted example, two ends of reaction vessel 264 are retained within respective slots 266 of rack 254, but in other examples, the rack may be configured to hold the reaction vessel in any other suitable manner. Rotation of rack 254 causes the reaction vessel to move in a circular path about shaft 258.

The motor coupled to shaft 258 is selectively driven by a motor controller (not shown), which may be coupled to and/or part of an electronic controller (not shown), such as control electronics 112, described above with reference to FIG. 1. The electronic controller is configured to selectively control the motor controller to drive the motor in accordance with a protocol. The protocol includes instructions (executable, e.g., by the electronic controller and/or a processor coupled to the electronic controller) that the motor be driven at a first speed in a first direction for a first time interval, at a second speed in a second direction for a second time interval, and so on, up to any suitable number of time intervals. In some examples, the protocol further includes instructions to adjust a temperature of the oven to a respective setpoint value during one or more of the intervals.

In the depicted example, oven 250 includes a manual motor speed control 270 coupled to the motor controller and configured to allow a user to manually adjust a motor speed and/or direction, and a manual temperature control 272 coupled to a heating element of the oven and configured to allow a user to manually adjust the oven temperature. In some examples, manual controls 270 and 272 may be configured to selectively override the electronic controller. Alternatively, or additionally, manual controls 270 and 272 may be configured to be disabled when the electronic controller is controlling the motor and heating element. In some examples, the manual controls are omitted.

Optionally, a thermometer configured to display an ambient oven temperature to a user may be disposed within oven interior 252. The oven may optionally further include a hygrometer and/or any other suitable sensors.

Figure 6:
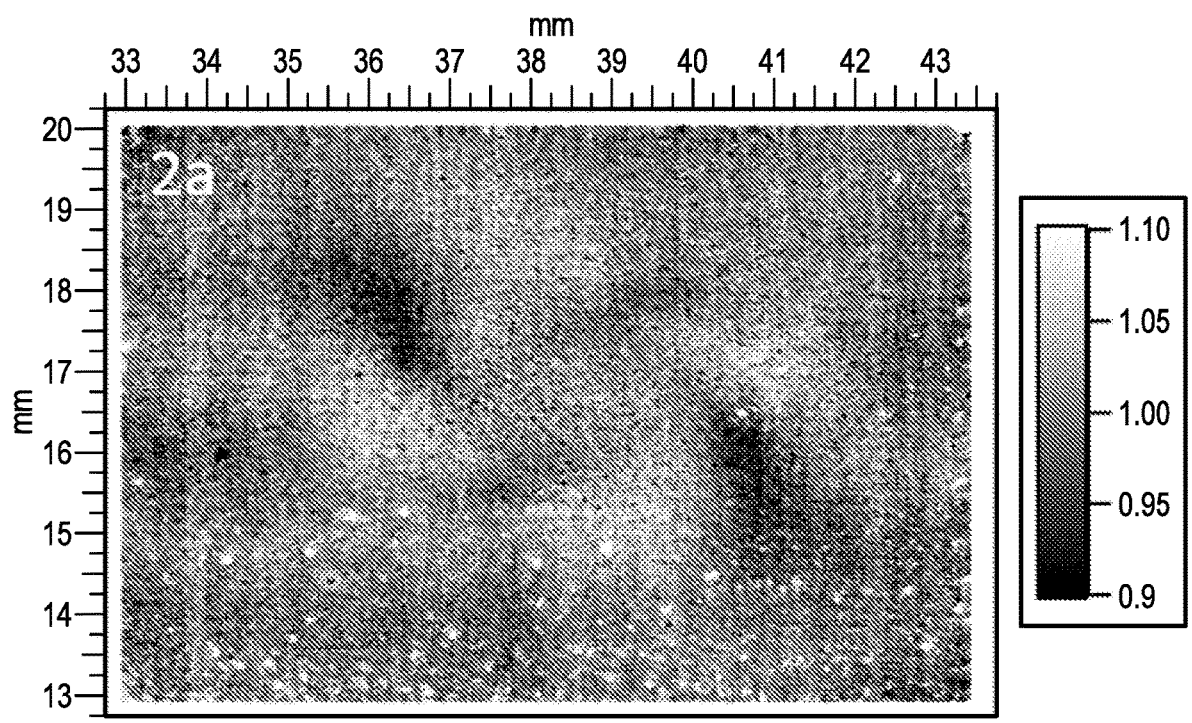
FIG. 6 is a comparison of a feature deviation ratio (FDR) map of data obtained using conventional methods and an FDR map of data obtained using an example of the system of FIG. 1, in accordance with aspects of the present teachings.
Figure 6:
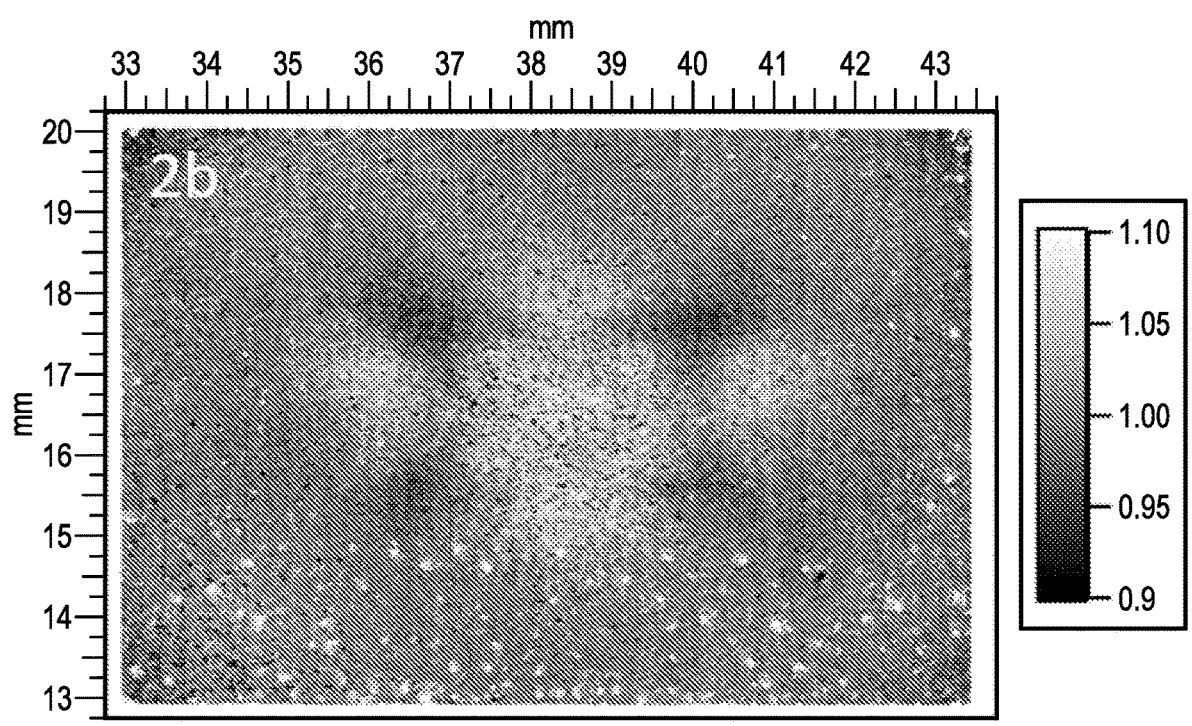

FIG. 6 depicts respective feature deviation ratio maps (explained further in Section B below) for each of two experiments. In map 2a, hybridization occurred under standard conditions, in which the reaction chambers were rotated at 20 rpm over a period of 19 hours. In map 2b, hybridization also occurred with rotation at 20 rpm over a period of 19 hours, but the direction of rotation was reversed at one minute intervals. The feature deviation ratio map is much more uniform in the second case (i.e., map 2b) than in the first (i.e., map 2a).

Figure 7:
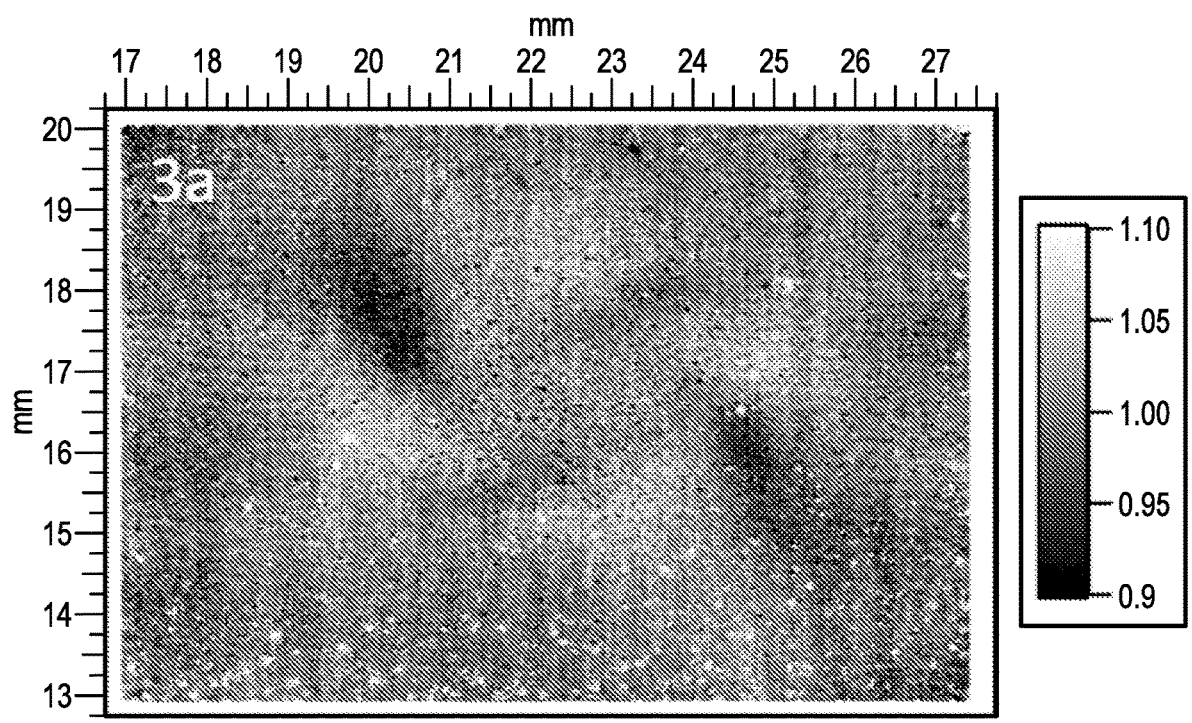
FIG. 7 is another comparison of a feature deviation ratio (FDR) map of data obtained using conventional methods and an FDR map of data obtained using an example of the system of FIG. 1, in accordance with aspects of the present teachings.
Figure 7:
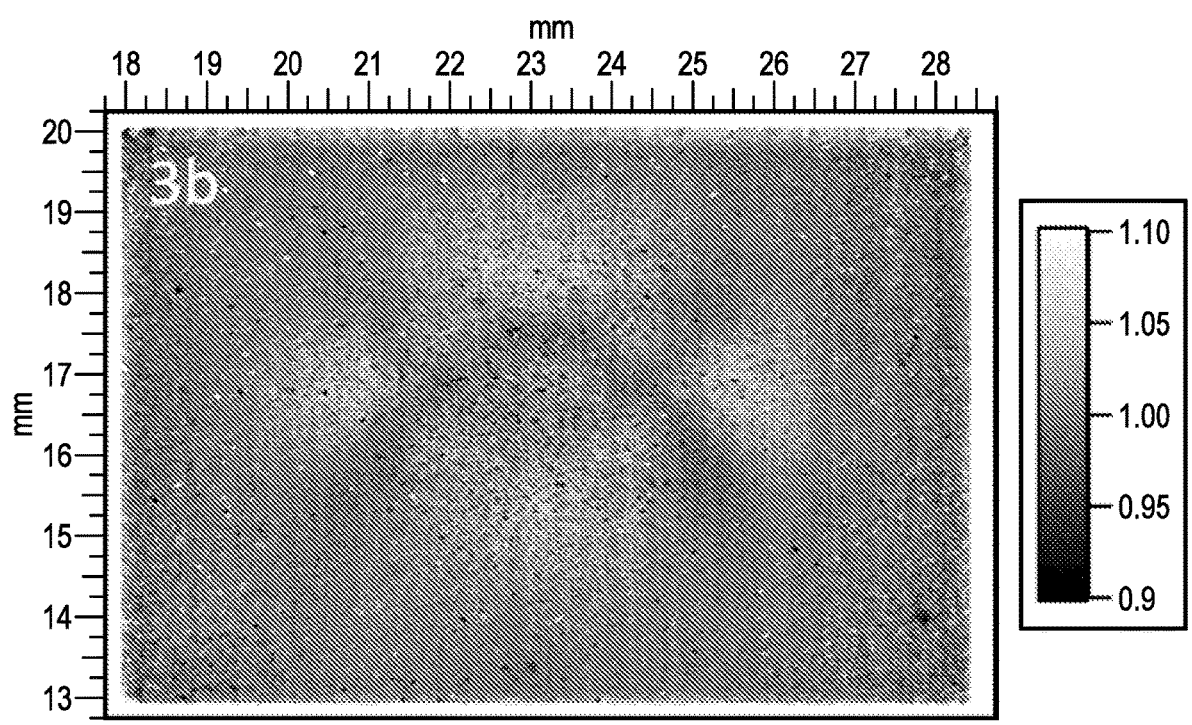

FIG. 7 depicts respective feature deviation ratio maps (explained further in Section B below) for each of two experiments. In map 3a, hybridization occurred under standard conditions, in which the reaction chambers were rotated at 20 rpm over a period of 19 hours. In map 3b, hybridization also occurred over a period of 19 hours, but at one minute intervals the direction of rotation was reversed and the rotation speed was changed to a randomly selected value between 20 rpm and 60 rpm (inclusive). The feature deviation ratio map is much more uniform in the second case (i.e., map 3b) than in the first (i.e., map 3a), and is also much more uniform than the second feature deviation map shown in FIG. 6 (i.e., map 2b).

B. Experimental Data Comparison—Change in Rotation Direction

Preliminary data obtained using an illustrative example of an automatically controlled mixing system in accordance with aspects of the present teachings demonstrates that the inclusion of at least one change in the direction of mixing of the reaction chamber (e.g., the direction of rotation of the reaction chamber) over the course of a reaction provides a modest decrease in time to completion and a surprisingly significant improvement in array uniformity.

To confirm the results, including the improved array signal and uniformity, experiments were conducted on microarrays purchased from various vendors (in this example, Agilent SurePrint G3 custom Microarrays). A first set of experiments was conducted with an exact same type of microarray using a standard, manually controlled hybridization oven (Agilent G2545A Hybridization Oven, speed set to 20 rpm, 55° C.) and a second set using an example of the automatically controlled oven described above (e.g., oven 125). Both sets of experiments used the same reaction mixture and reaction chamber assembly. Reactions took place over a 19-hour period. Over the course of the 19-hour reaction period, the automatically controlled reaction oven was automatically controlled to automatically vary the direction of mixing at one-minute intervals over the course of the reaction period. The automatically controlled oven maintained the same environmental conditions as the standard oven, such as an oven temperature of 55° C., etc. The automatically controlled oven was programmed to maintain the same rate of rotation of the rack as the standard oven in between changes of direction of mixing, namely 20 rpm. After the reaction slides were washed and dried, they were scanned using an Agilent SureScan Microarray Scanner G4900DA using embedded protocols for scanning molecules tagged with cyanine-3 fluorescent labels.

Methods for evaluating array uniformity were developed to assess the impact of automatic changes of mixing direction on array uniformity. One novel evaluation method includes the evaluation of a "feature deviation ratio" (FDR). This metric relies on replicate reactions of the same probe molecule on an array, subarray, or the like. A replicate in this context is a feature composed of identical probe molecules to other features (i.e., such that a set of replicates is a set of features all having the same probe molecule composition). Typically, 3-20 replicates for each probe molecule are found in an array, from which an average or median may be calculated, typically after rejecting replicates that deviate too far from the mean. A low degree of deviation between replicates increases confidence in the averaged result over all replicates. The respective fluorescence-scan signals of all of the replicates of a same type are aggregated into a population. The median signal of the population is calculated. The FDR of each replicate is obtained by dividing the replicate's signal by the median signal of the associated population. The FDR of each replicate within a population is calculated. If there is more than one type of replicate (e.g., more than one population) on an array (or subarray, or other suitable unit), a respective FDR is calculated for each replicate of each type based on the median signal of the respective population.

Implementation of this feature-by-feature FDR is most efficacious when all (or a subset) of the FDRs are either accumulated into a mathematical distribution or mapped onto the spatial pattern formed by replicates of the array (or subarray, or other suitable unit). "FDR maps" involve calculating a feature-by-feature FDR for all molecular features organized in the array, subarray, or the like. The scanned image of the array is analyzed by software to extract signals from tagged molecules. Feature deviation ratios are calculated for each population using these signals. The FDR metric has utility beyond mapping and population distribution analysis.

In the experiment described above, the FDR metrics were applied. Surprisingly, for reaction periods during which the direction of mixing (e.g., direction of rack rotation) changed at one-minute intervals, a large improvement in signal uniformity was observed based on the FDR metrics. FIG. 6 depicts respective FDR maps of data obtained using standard rotational mixing (graph 2a) and data obtained using rotational mixing with the direction of rotation changing at one-minute intervals (graph 2b). In graphs 2a and 2b, the horizontal axes represent spatial position on a microarray, and the intensity represents FDR. The FDR maps of FIG. 6 correspond to arrays reacted with the same solution and environmental conditions, such that the change in rotation direction of graph 2b is the primary or only difference between the data sets from which the two maps were calculated. In FIG. 6 the reaction mixture was reacted with the array using an Agilent G2545A Hybridization Oven, speed set to 20 rpm, 55° C. In graph 2b, the reaction mixture was reacted with the array using a version of the automatically controlled oven programmed to change the direction of mixing at least once over the course of the reaction. In graph 2a, the direction of mixing did not change during the course of the reaction. The greater spatial uniformity in the FDR map of graph 2b corresponds to a greater uniformity of reactions caused by the change in the direction of mixing (e.g., of rotation of the rack).

As FIG. 6 shows, comparing the FDRs reveals an improvement in reaction uniformity when the rotation direction is changed at one-minute intervals. The FDR maps of FIG. 6 (gray scale range of 0.9 to 1.1) show a reduction in reaction artifacts and an increased number of reaction sites colored gray rather than black or white (reporting within ±10% of their population median) when the direction of rotation changes at one-minute intervals during the reaction period (corresponding to graph 2b in FIG. 6). Numerical analysis of the distribution of reaction sites demonstrates a surprising increase in array uniformity with the inclusion of a direction change, with the percentage of reaction sites signaling within ±5% of their population median (and thus falling within an FDR Range of 0.95 to 1.05) increasing from ~85% to >95%.

These data suggest that even a single change in direction of rotation, for instance in the middle of the course of the reaction, could show a significant improvement in reaction uniformity. Likewise, other protocols involving changing the direction of rotation at time intervals other than one-minute intervals could also show a significant improvement in reaction uniformity.

C. Illustrative Method—Change in Rotation Speed

Section B above describes illustrative experiments including at least one change in the direction of mixing of a reaction chamber (e.g., the direction of rotation of the reaction chamber) over the course of a reaction, with a rotation speed of the chamber remaining constant. In some other illustrative examples in accordance with aspects of the present teachings, the rotation speed of the chamber is changed at least once over the course of the reaction and the rotation direction remains constant. For example, the rotation speed may be changed at one-minute intervals.

D. Experimental Data Comparison—Change in Rotation Speed and Direction

Preliminary data obtained using an example of an automatically controlled mixing system in accordance with aspects of the present teachings demonstrates that the inclusion of at least one change in the rate of mixing of the reaction chamber (i.e., the rate of rotation of the reaction chamber) as well as at least one change in the direction of mixing (i.e., the direction of rotation of the reaction chamber) over the course of a reaction provides a surprisingly large improvement in array uniformity.

To confirm the results, including the improved array signal and uniformity, experiments were conducted on microarrays purchased from various vendors (in this example, Agilent SurePrint G3 custom Microarrays). A first set of experiments was conducted with an exact same type of microarray using a standard, manually controlled hybridization oven (Agilent G2545A Hybridization Oven, speed set to 20 rpm, 55° C.) and a second set of experiments using an example of the automatically controlled hybridization oven described above (e.g., oven 125). Both sets of experiments used the same reaction mixture and reaction chamber assembly. Reactions took place over a 19-hour period. Over the course of the reaction period, the automatically controlled reaction oven was automatically controlled to, at one-minute intervals, change both the direction and speed of rotation. The automatically controlled oven maintained the same environmental conditions as the standard oven, such as temperature at 55° C., etc. After the reaction slides were washed and dried they were scanned using an Agilent SureScan Microarray Scanner G4900DA using embedded protocols for scanning molecules tagged with cyanine-3 fluorescent labels.

Data obtained in the experiment described above was analyzed using FDR metrics. FIG. 7 depicts FDR maps of arrays from the experiment (gray scale range of 0.9 to 1.1). In the map 3a, the reaction mixture was reacted with the array using a standard manually controlled Agilent G2545A Hybridization Oven, speed set to 20 rpm, 55° C. In map 3b, the reaction mixture was reacted with the array using the automatically controllable oven programed to change the direction of mixing and speed of mixing at one-minute intervals over the course of the reaction. In both the standard manually controlled oven and the automatically controlled oven, the arrays were reacted with the same solution and environmental conditions. Surprisingly, a significant improvement in signal uniformity was observed based on changing the direction and speed of rotation at one-minute intervals during the same reaction. Comparison of FDR maps using standard rotational mixing (map 3a) and rotational mixing with changes in speed and direction at one-minute intervals (map 3b) demonstrates an improvement in reaction uniformity. The map reveals a reduction in reaction artifacts and an increased number of reaction sites colored gray rather than black or white (reporting within ±10% of their population median) with changes at one-minute intervals in rotation direction and speed. Numerical analysis of the distribution of reaction sites demonstrates a surprising increase in array uniformity from ~85% to >98% of reaction sites signaling within ±5% of their population median with these changes.

These data suggest that even a single change in direction of rotation combined with even a single change in rotation speed, for instance in the middle of the course of the reaction, could show a significant improvement in reaction uniformity. Likewise, other protocols involving changing the direction of rotation combined with changing the rotation speed to variable values at different time intervals could also show a significant improvement in reaction uniformity.

FDR maps may vary from microarray to microarray, even for those located on the same solid surface (e.g., subarrays on a same microarray slide) which are ostensibly exposed to identical conditions (same temperature, rotation rate, etc.). These variations may arise because subarrays may not be placed identically within a reaction chamber, because the reaction chambers themselves may not be identical nor located at identical distances from the axis of rotation, and/or because the sample fluid and/or bubble volume may not be identical, all of which may lead to different mixing patterns (and thus to different FDR maps).

Despite these variations, there are characteristic mixing patterns, revealed by FDR mapping, that are formed due to rotation rate and direction. In particular, if the width of the mixing chamber is significantly different from the length, then the FDR map shows symmetry across one or more diagonal axes and does not show vertical or horizontal symmetry. If the direction of rotation is reversed, the characteristic mixing pattern becomes reflected across the horizontal axis (or identically across the vertical axis). Changing the rotation rate modifies aspect(s) of the characteristic mixing pattern while maintaining the overall characteristic form (e.g., a general shape of the distinctive feature(s) of the FDR map), until the point at which the centrifugal force due to rotation approaches the force of gravity, at which point buoyancy is decreased or lost, and the bubble no longer makes full rotations of the mixing chamber. In these cases, large dark regions occur in the FDR maps, corresponding to areas closer to the axis of rotation, where the bubble is trapped and sample fluid does not make contact with the microarray.

Figure 13:
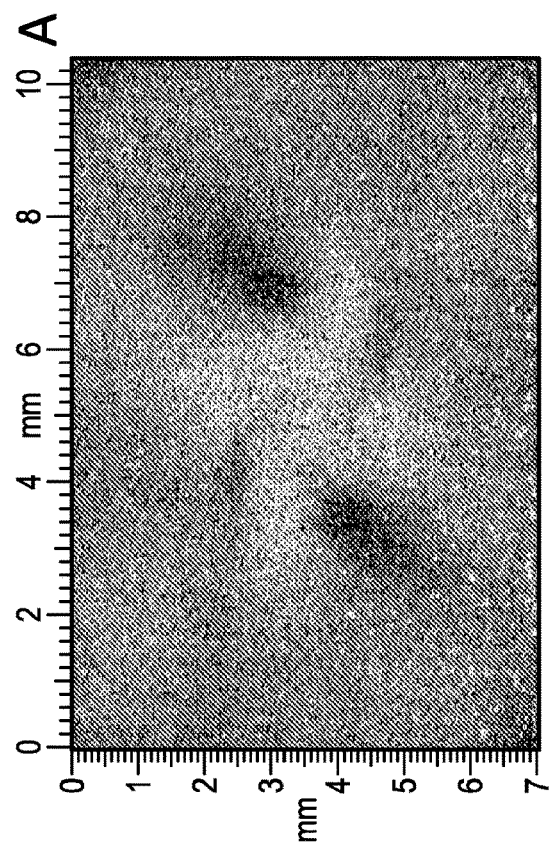
FIG. 13 is a set of feature deviation ratio (FDR) maps depicting an illustrative superposition (map C) of FDR maps associated with simple mixing protocols (maps A and B) suitable for use in predicting an FDR map (map D) associated with a more complex protocol, in accordance with aspects of the present teachings.
Figure 13:
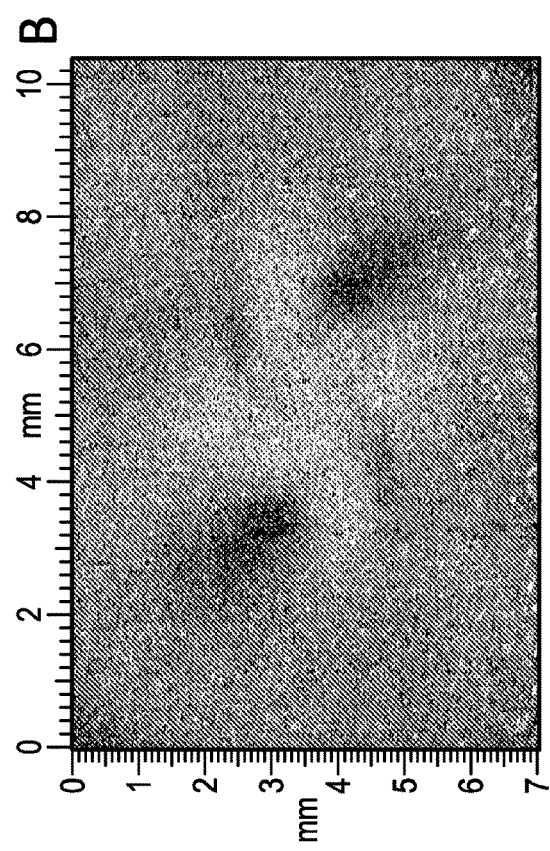
Figure 13:
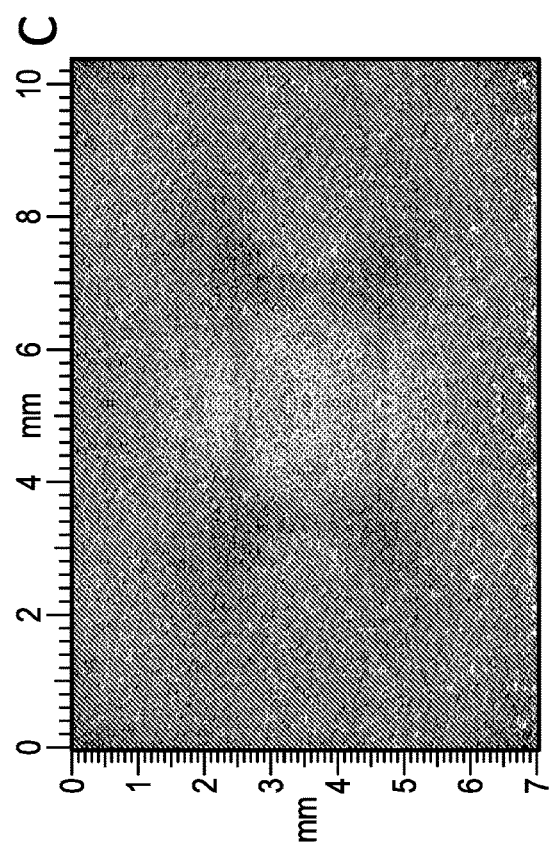
Figure 13:
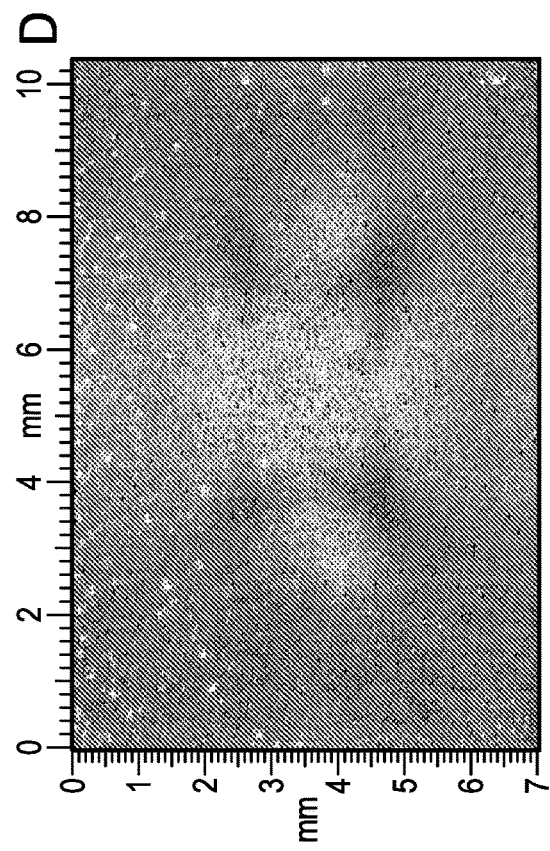

The FDR map that results from changing from a first condition to a second condition (e.g., changing from a first rotation rate and/or direction to a second rotation rate and/or direction) during a mixing period can be predicted by a linear superposition of FDR maps generated under each of the different conditions, weighted by the relative time spent under each condition. An illustrative example is illustrated by FIG. 13. In FIG. 13, Map A is the FDR map for a sample rotated at a constant rotation rate of 20 rpm with no change in direction. Map B is Map A flipped across a vertical axis, corresponding to a theoretical prediction of the FDR map that would be obtained by rotating the sample of Map A at a constant rate of 20 rpm in the opposite rotational direction from the rotational direction associated with Map A. Map C is a linear superposition of Map A and Map B with equal weighting of Map A and Map B. Map D is the FDR map for a sample rotated at a constant rate of 20 rpm with the direction of rotation reversed every 60 seconds. Maps C and D show a close correspondence, showing that Map D can be predicted with high accuracy by the linear superposition of Map A and Map B. That is, the FDR map associated with a sample for which the direction of rotation is reversed every 60 seconds (and the rotational speed is a first constant rotational speed) is well approximated by the linear superposition of an FDR map associated with a sample with a first constant direction of rotation and an FDR map associated with a sample with a second constant direction of rotation opposite the first constant direction (with the two samples of the superposition being rotated at the first constant rotational speed).

Experiments have shown that the relative time that a feature has spent in contact with the sample fluid (e.g., as a percentage of the overall reaction time) has some correlation with FDR. A mapping of relative time of sample fluid contact to feature position is called a fluid residence time (FRT) map. Other experiments have shown support for the proposition that the bulk velocity of the fluid in contact with the feature has some correlation with FDR as well. A mapping of the bulk fluid velocity averaged over time (in which the bulk fluid velocity is assumed to be zero in the absence of fluid) is called an Averaged Fluid Velocity (AFV) map. In both these cases, experimental data was obtained by video capture of mixing in a reaction chamber using a camera fixed in the reference frame of rotation shared with the reaction chamber.

Figure 14:
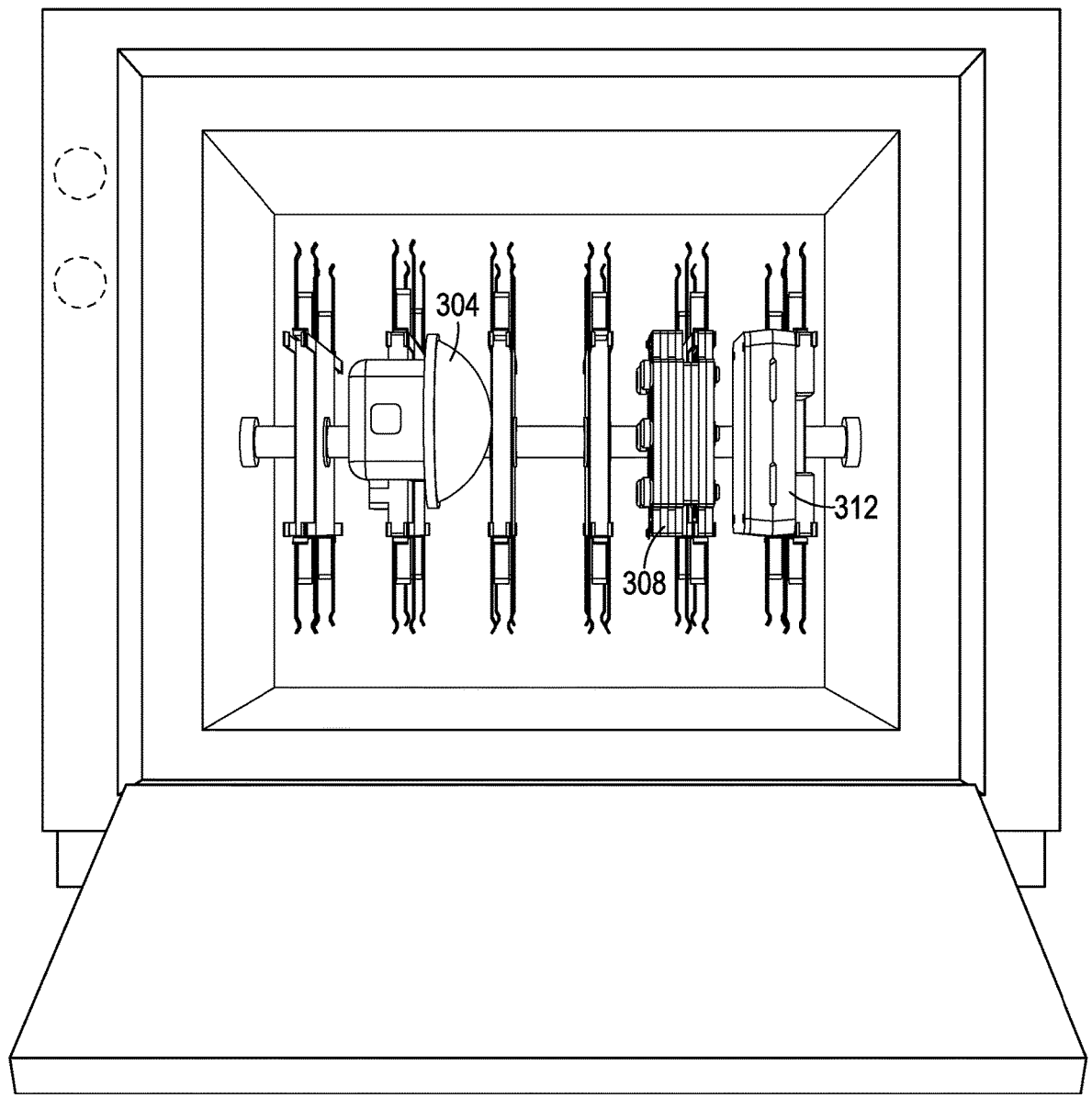
FIG. 14 is a front view of an illustrative assembly including a camera and lightbox configured for video capture of fluid movement within an illustrative reaction vessel in a hybridization oven, in accordance with aspects of the present teachings.

FIG. 14 shows the video setup assembly used for the video capture. A reaction vessel 308 is mounted on a rotatable rack within a hybridization oven with a video camera 304 positioned to record images from the front side of the reaction vessel and a light box 312 positioned to illuminate the reaction chamber from the back side of the reaction vessel. Vessel 308 is configured such that the reaction chambers of the vessel are visible from the front side, such that the reaction chambers can be imaged by the camera, and to be at least partially transparent and/or translucent from the back side such that the light box behind the vessel illuminates the reaction chamber to facilitate imaging by the camera. Diffuser plates and/or panels configured to produce a uniform illumination may optionally be placed between the light box and the reaction vessel. Some diffuser plates may optionally be placed in direct contact with the light box; additionally or alternatively, diffuser panels may optionally be directly incorporated into the reaction vessel.

Figure 15:
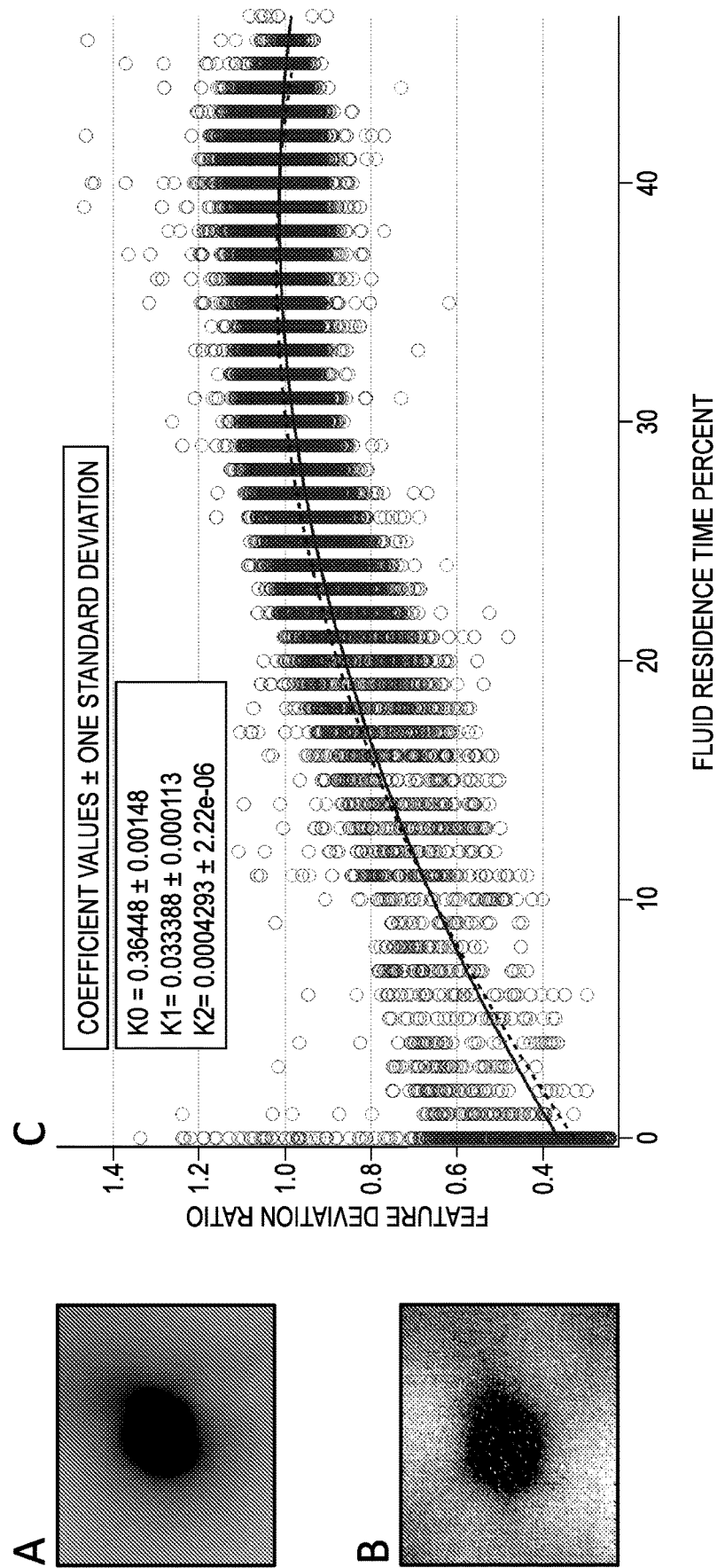
FIG. 15 is a fluid residence time (FRT) map (A) compared with a feature deviation ratio FDR map (B), and a plot depicting FDR values plotted against FRT values, in accordance with aspects of the present teachings.

In one experiment showing a correlation between fluid residence time (FRT) and FDR mapping, blue food coloring was added to a sample volume which was subjected to a 19 hour hybridization reaction with a rotational velocity of 20 rpm in one direction of rotation at 55° C., as described above. At one hour into the reaction, by which temperature equilibration can be assumed to have been achieved, a 30 second video was captured, using a video setup as described above with reference to FIG. 14. The presence of the fluid for each pixel in each frame of the video was determined over five full rotations, which allowed for calculation of the FRT map. A FDR map was also generated as described above, and the FRT value for each feature of the FDR map was determined based on the corresponding pixels in the FRT map. FIG. 15 depicts the generated FRT map (map A) for the subarray area, the associated FDR map (map B), and a plot of the FDR values vs. the FRT values (plot C).

In one experiment showing a correlation between averaged fluid velocity (AFV) and FDR mapping, colored neutral buoyancy beads, having a density matched to that of the sample fluid, were introduced into a sample fluid that had been dyed for easier tracking, and five minutes of video was captured, using a video setup as described above with reference to FIG. 14. Image analysis was used to determine the position of each bead in each frame of the video over several rotations, as well as the presence or absence of fluid in each pixel of each frame. The velocity of each bead was determined by measuring the displacement of each bead between consecutive video frames (anomalous results were rejected), and these velocities were taken as proxies for the bulk fluid velocity at the midpoint of each bead trajectory. The resulting AFV maps displayed profiles characteristic of those of FDR maps corresponding to similar conditions.

E. Illustrative Method of Facilitating a Reaction within a Reaction Chamber

Figure 8:
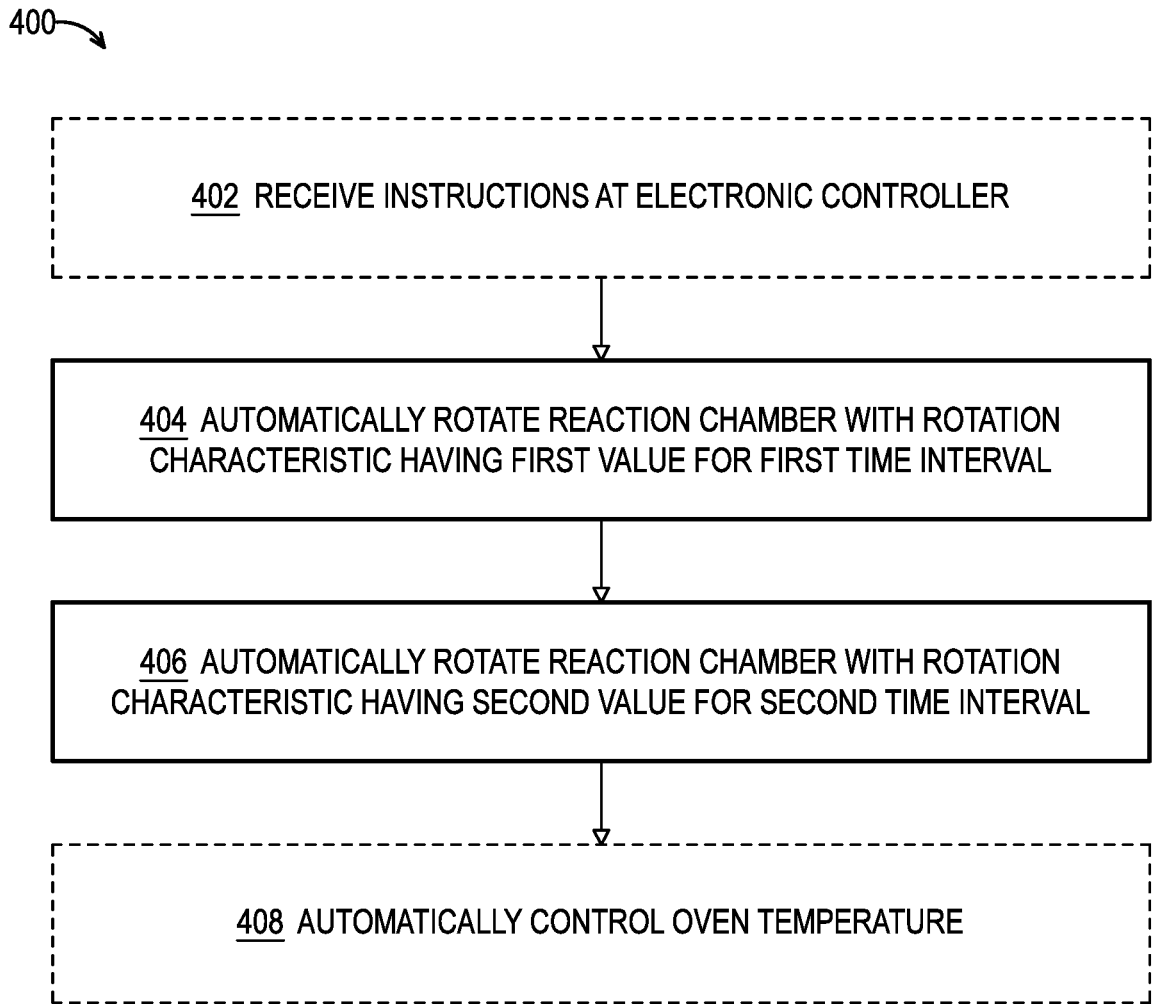
FIG. 8 is a flow diagram depicting steps of an illustrative method for facilitating a reaction within a reaction chamber with improved uniformity, in accordance with aspects of the present teachings.

This section describes steps of an illustrative method 400 for facilitating a reaction within a reaction chamber with increased uniformity; see FIG. 8. Aspects of reaction chamber assemblies and automatically controllable hybridization ovens described elsewhere herein may be utilized in the method steps described below. Where appropriate, reference may be made to components and systems that may be used in carrying out each step. These references are for illustration, and are not intended to limit the possible ways of carrying out any particular step of the method.

FIG. 8 is a flowchart illustrating steps performed in an illustrative method, and may not recite the complete process or all steps of the method. Although various steps of method 400 are described below and depicted in FIG. 8, the steps need not necessarily all be performed, and in some cases may be performed simultaneously or in a different order than the order shown.

At step 402, method 400 optionally includes receiving, at an electronic controller, machine-executable instructions to rotate a rack during a first time interval and during a second time interval, such that a characteristic of the rotation has a first value during the first interval and a second value during the second interval, the second value being different from the first. For example, the characteristic may be rotational speed of the rack, and the first and second values may be different speeds. In other examples, the characteristic may be a direction of rotation, and the first and second values are opposing directions. In some examples, the instructions are configured are configured to cause the rack to be rotated at a first speed in a first direction during the first interval, and at a second speed in a second direction during the second interval, with second speed being different from the first speed and the second direction being different from the first direction.

At step 404, method 400 includes automatically rotating the reaction chamber (e.g., by automatically rotating the rack) for the first time interval such that the characteristic of the rotation has the first value. The rack holds a reaction chamber that is mixed by the rotational motion. In examples wherein step 402 is performed, step 402 is performed prior to step 404, and the automatic rotation of the rack at step 404 is performed based on the instructions received at step 402.

The reaction chamber is a sealed container configured to hold a fluid such that the fluid can pass over a surface of the reaction chamber. One or more molecules are attached to the surface of the reaction chamber and configured to bind with one or more specific types of reactants within the fluid. The reaction chamber may be coupled to the rack in any suitable manner. In some examples, the reaction chamber is formed by a microarray slide, a gasket and a cover slide, and the microarray slide and cover slide are clamped together in a reaction vessel assembly. One or more additional reaction chambers may be formed by the microarray slide, cover slide, and additional gasket(s).

The rack may comprise any suitable device for holding the reaction chamber such that the reaction chamber is rotatable. In some examples, the rack includes one or more attachment devices (e.g., slots, clamps, receptacles, threaded bores and/or fasteners, pockets, and/or any other suitable devices) configured to hold the reaction chamber (e.g., to hold a reaction vessel assembly including the reaction chamber). The rack is configured to hold the reaction chamber such that rotation of the rack about its rotational axis moves the reaction chamber in a path about the rotational axis, facilitating movement of the fluid within the reaction chamber relative to the reaction surface within the reaction chamber. In some examples, the rack is disposed within a hybridization oven or other suitable reaction oven.

Automatically rotating the rack includes causing a drive motor coupled to the rack to rotate the rack about its rotational axis. The drive motor is controlled by an electronic controller configured to drive the motor based on the instructions optionally received at step 402, which are stored in a memory coupled directly or indirectly to the electronic controller. In examples where step 402 is omitted, the instructions may be preloaded into memory accessible to the electronic controller.

In this example, the instructions include instructions to drive the motor such that a characteristic of the rotation of the rack (e.g., a rotation speed or direction) has a first value (e.g., a first speed or first direction) for the first time interval. The instructions include information sufficient to cause the motor to rotate the rack such that the characteristic has the first value. The information may include a motor speed, torque, current, direction, and/or any other suitable parameter(s). The instructions further include the duration of the first time interval and/or an end time of the first time interval. In other examples, however, the instructions may be configured to calculate one or more of the first value and the first time interval based on sensed data about the reaction chamber (e.g., sensed data corresponding to the reaction taking place within the reaction chamber) and/or any other suitable data.

At step 406, method 400 includes automatically rotating the rack for a second time interval such that the rotation characteristic has a second value. Rotating the rack at step 406 includes driving the motor such that the rotation characteristic has the second value (e.g., a speed or direction different from the speed or direction of the first time interval). The rack may be rotated based on instructions preloaded into memory accessible by the electronic controller, based on instructions received at step 402 (i.e., prior to the beginning of the first time interval), based on instructions received sometime after the beginning of the first time interval, and/or any other suitable instructions. The instructions may be expressed as a desired motor speed and/or direction, as an adjustment to be made to the motor speed and/or direction used in the first time interval, and/or in any other suitable manner.

Method 400 may further include rotating the rack at one or more further time intervals at respective rotational speeds and directions. The speed corresponding to each time interval may or may not be different from the speed corresponding to the previous interval, and the direction corresponding to each time interval may or may not be different from the direction corresponding to the previous interval. Put another way, the speed and direction do not necessarily change at each interval.

At step 408, method 400 optionally includes automatically controlling a temperature of a reaction oven within which the rack is disposed. The temperature may be automatically controlled by the same electronic controller as the drive motor (e.g., by a same processor, and/or by a different processor within a same control assembly), by a different controller, and/or by any other suitable arrangement. Automatically controlling the temperature may include automatically controlling a heating element of the oven to maintain a sensed oven temperature at a selected setpoint. In some examples, the instructions executed by the controller (e.g., the instructions received at step 402, and/or any other suitable instructions) specify a setpoint temperature for each of the first time interval, second time interval, and any further time intervals (e.g., the protocol may include a setpoint temperature for each time interval). The setpoint temperature corresponding to each time interval may or may not be different from the setpoint temperature corresponding to the previous interval.

F. Illustrative Method of Controlling a Hybridization Oven

Figure 9:
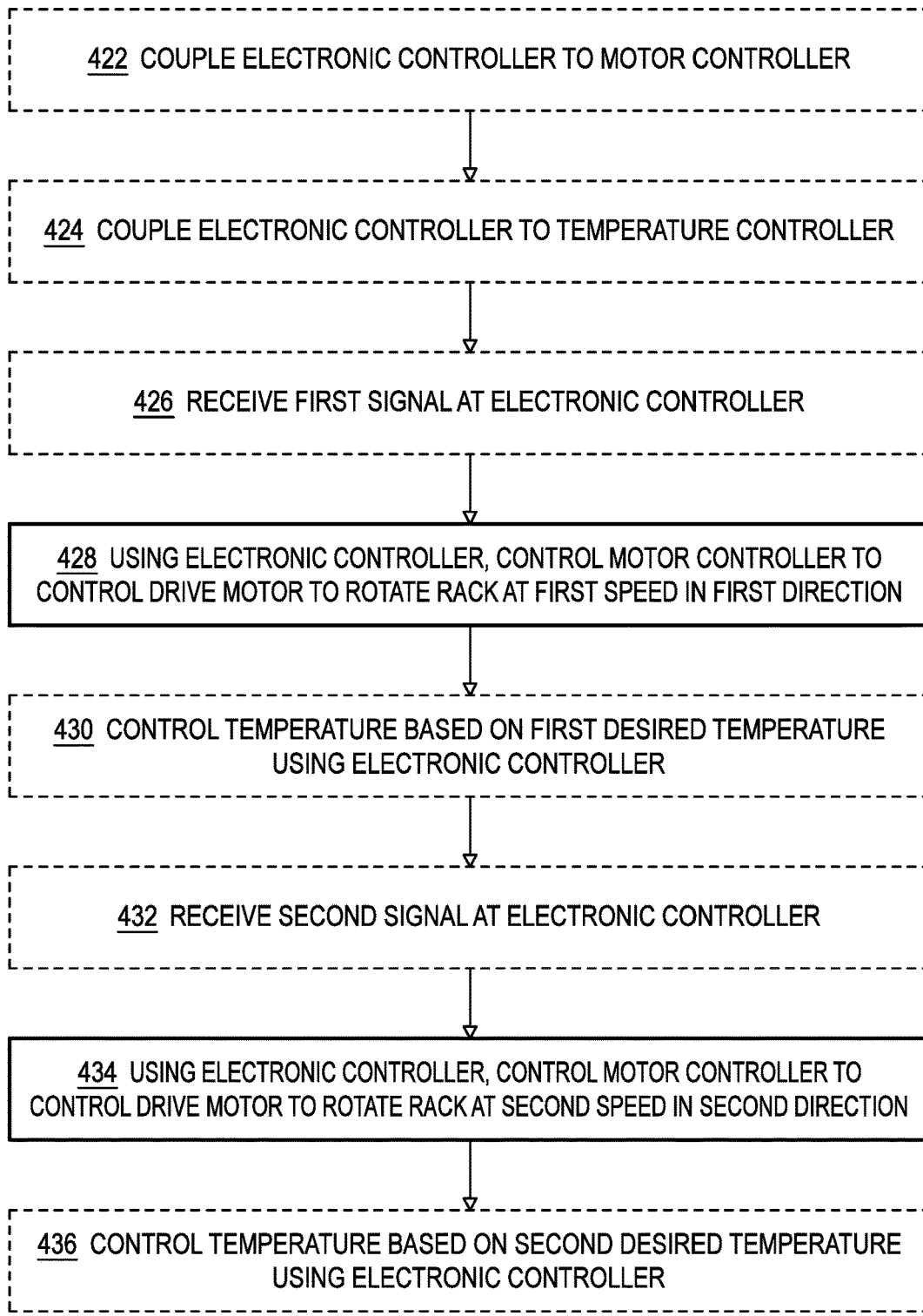
FIG. 9 is a flow diagram depicting steps of an illustrative method for controlling a hybridization oven, in accordance with aspects of the present teachings.

This section describes steps of an illustrative method 420 for controlling a hybridization oven; see FIG. 9. Aspects of reaction chamber assemblies and hybridization ovens described elsewhere herein may be utilized in the method steps described below. Where appropriate, reference may be made to components and systems that may be used in carrying out each step. These references are for illustration, and are not intended to limit the possible ways of carrying out any particular step of the method.

FIG. 9 is a flowchart illustrating steps performed in an illustrative method, and may not recite the complete process or all steps of the method. Although various steps of method 420 are described below and depicted in FIG. 9, the steps need not necessarily all be performed, and in some cases may be performed simultaneously or in a different order than the order shown.

At step 422, method 420 optionally includes coupling an electronic controller to a motor controller coupled to a drive motor, the drive motor being configured to rotate a rack or other suitable device in a hybridization oven (or other suitable reaction oven). The electronic controller may comprise any suitable processing logic configured to control the motor controller to selectively control the drive motor.

At step 424, method 420 optionally includes coupling the electronic controller to a temperature controller of the oven. The temperature controller may comprise any suitable processing logic configured to control the temperature of the oven (e.g., by controlling a heating element of the oven to maintain the oven temperature at a desired setpoint).

Steps 422 and 424 are optional and may be omitted if, e.g., the electronic controller is already coupled to motor controller or temperature controller, respectively.

At step 426, method 420 optionally includes receiving, at the electronic controller, a first signal configured to cause the electronic controller to control the motor controller to control the drive motor to rotate the rack at a first predetermined speed and in a first predetermined direction. In some examples, the electronic controller is configured to receive the first signal from a computer or other suitable processor configured to access instructions stored in a memory device, the signal being based on the stored instructions. The instructions comprise a protocol including, for each of a plurality of time intervals, information corresponding to a desired rotation speed and direction of the rack. The information corresponding to the desired rack rotation speed and direction may be expressed as an actual rotation speed and direction of the rack, as a speed and direction of the motor that correspond to the desired speed and direction of the rack, as a motor torque and/or current corresponding to the desired speed and/or direction of the rack, and/or in any other suitable manner. The electronic controller is configured to determine, based on the received first signal corresponding to the instructions, an appropriate signal to transmit to the motor controller to cause the motor to rotate the rack at the desired rack rotation speed and direction.

Step 426 may be omitted in examples where, e.g., it is unnecessary to receive the instructions at the electronic controller (for example, if instructions are preloaded into a memory device of the electronic controller).

At step 428, method 420 includes controlling the motor controller based on the first signal using the electronic controller (e.g., by transmitting an appropriate signal from the electronic controller to the motor controller) to control the drive motor to rotate the rack at the first predetermined speed and in the first predetermined direction.

At step 430, method 420 optionally includes controlling the temperature controller using the electronic controller to control the oven temperature at a first desired temperature. The electronic controller may be configured to control the oven controller based on instructions received by the electronic controller from a stored memory, from a computer or other suitable processor in communication with the electronic controller, from a user interface device configured to receive user input, and/or from any other suitable source. In some examples, the electronic controller is configured to control the oven temperature to the first desired temperature based on the first signal (i.e., the first signal may be configured to cause the electronic controller to control the temperature controller as well as the motor controller). For example, the protocol including rotation information for the rack for each of a plurality of time intervals may also include temperature information for each time interval. Alternatively, the electronic controller may be configured to control the temperature controller in response to a different signal received from the same source as the first signal, and/or a different source.

At step 432, method 420 optionally includes receiving, at the electronic controller, a second signal configured to cause the electronic controller to control the motor controller to control the drive motor to rotate the rack at a second predetermined speed and in a second predetermined direction. Either the second predetermined speed is different from the first predetermined speed, the second predetermined direction is different from the first predetermined direction, or both.

In some examples, step 432 is omitted, and the first signal received at step 426 is configured to cause the electronic controller to control the drive motor (e.g., via the motor controller) to rotate the rack at the first predetermined speed in the first predetermined direction and then to rotate the rack at the second predetermined speed in the second predetermined direction. Put another way, the instruction to rotate the rack at the first speed and first direction and then at the second speed and second direction (and optionally, at yet other speeds and directions) may be embodied in one signal.

At step 434, method 420 includes controlling the motor controller using the electronic controller (e.g., by transmitting an appropriate signal from the electronic controller to the motor controller) to control the drive motor to rotate the rack at the second predetermined speed and in the second predetermined direction. In examples wherein a second signal is received at step 432, step 434 includes controlling the motor controller based on the second signal.

At step 436, method 420 optionally includes controlling the temperature controller using the electronic controller to control the oven temperature to a second desired temperature, which may be different from or equal to the first desired temperature. In some examples, the electronic controller is configured to control the oven temperature to the second desired temperature based on the second signal (e.g., the second signal includes instructions to control the temperature to the second desired temperature). Alternatively, the electronic controller may be configured to control the oven temperature to the second desired temperature based on the first signal, a different signal received from the same source as the second signal, and/or a different source, and/or on any other suitable basis.

In some examples, method 420 additionally includes rotating the rack (and optionally controlling the temperature) at one or more additional time intervals. For these additional time intervals, the speed corresponding to each time interval may or may not be different from the speed corresponding to the previous interval, and the direction corresponding to each time interval may or may not be different from the direction corresponding to the previous interval, and the temperature corresponding to each time interval may or may not be different from the temperature corresponding to the previous interval. Put another way, the speed, direction, and temperature do not necessarily change at each interval.

Figure 16:
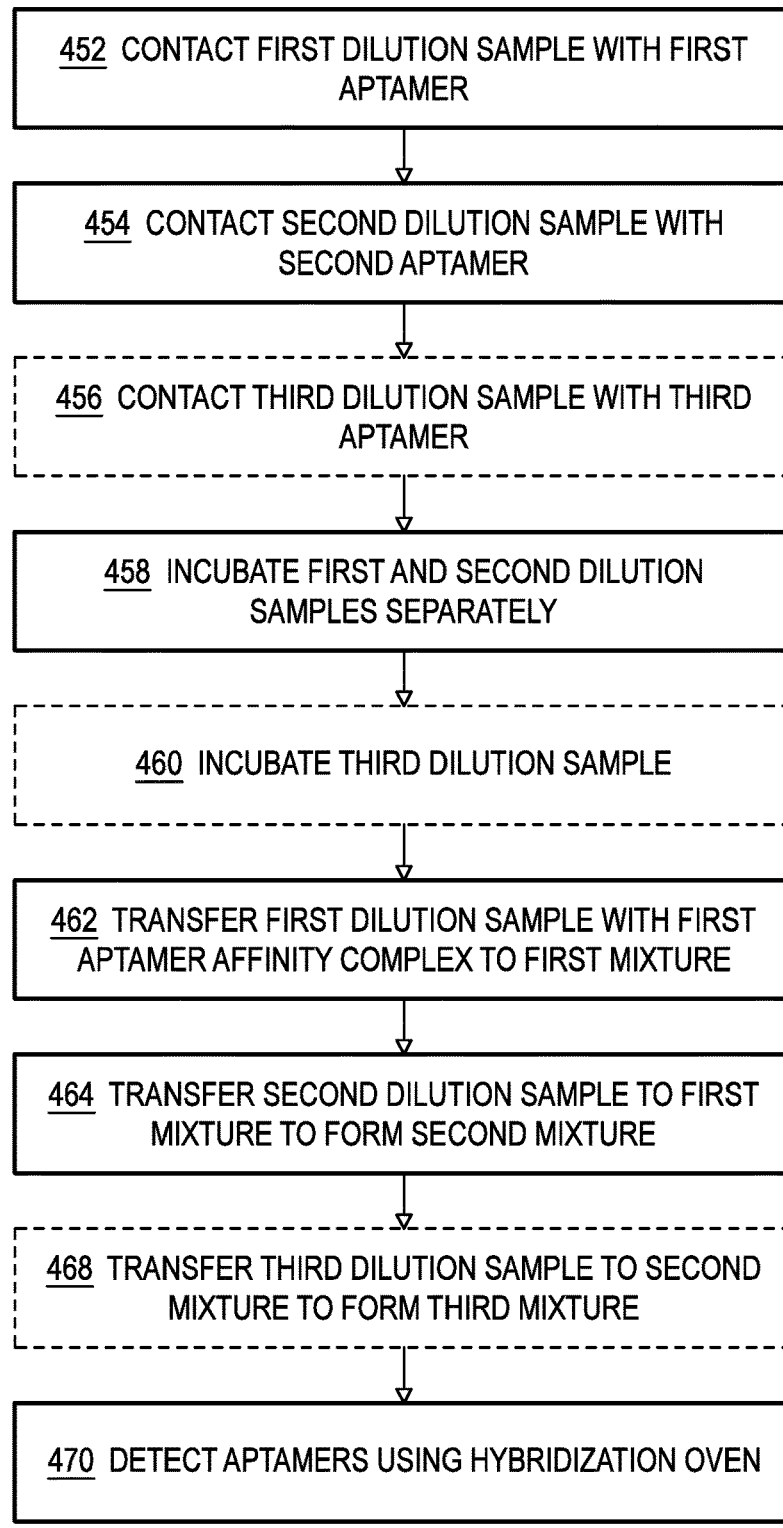
FIG. 16 is a flow diagram depicting steps of an illustrative method for an aptamer-based proteomics assay with improved readout utilizing the nucleic-acid nature of aptamers, in accordance with aspects of the present teachings.

G. Illustrative Method for Aptamer-Based Proteomics Assay with Improved Readout This section describes steps of an illustrative method 450 (see FIG. 16) for an aptamer-based proteomics assay with improved readout utilizing the nucleic-acid nature of aptamers. Method 450 is an illustrative example of a method that may be performed using an automatically controlled reaction oven in accordance with aspects of the present teachings. Aspects of systems and methods described elsewhere herein may be utilized in the method steps described below. Where appropriate, reference may be made to components and systems that may be used in carrying out each step. These references are for illustration, and are not intended to limit the possible ways of carrying out any particular step of the method.

In general, in a multiplex assay format where multiple target proteins are being measured by multiple capture reagents, the natural variation in the abundance of the different target proteins can limit the ability of certain capture reagents to measure certain target proteins (e.g., high abundance target proteins may saturate the assay and prevent or reduce the ability of the assay to measure low abundance target proteins). To address this variation in the biological sample, the aptamer reagents may be separated into at least two different groups (Capture Reagents for DIL1 and Capture Reagents for DIL2), preferably three different groups (A1—Capture Reagents for DIL1; A2—Capture Reagents for DIL2 and A3—Capture Reagents for DIL3), based on the abundance of their respective protein target in the biological sample. Each of the capture reagent groups, A1, A2 and A3 each have a different set of aptamers, with the aptamers having specific affinity for a target protein. The biological sample is diluted into two (Dilution 1 or DIL1 and Dilution 2 or DIL2), preferably three, different dilution groups (Dilution 1 or DIL1; Dilution 2 or DIL2 and Dilution 3 or DIL3) to create separate test samples based on relative concentrations of the protein targets to be detected by their capture reagents. Thus, the biological sample is diluted into high, medium and low abundant target protein dilution groups, where the least abundant protein targets are measured in the least diluted group, and the most abundant protein targets are measured in the greatest diluted group. The capture reagents for their respective dilution groups are incubated together (e.g., the A1 set of aptamers are incubated with the test sample of Dilution 1 or DIL1; the A2 set of aptamers are incubated with the test sample of Dilution 2 or DIL2 and the A3 set of aptamers are incubated with the test sample of Dilution 3 or DIL3). The total number of aptamers for A1, A2 and A3 may be 7,000; 7,500; 8,000 or more aptamers.

Figure 10:
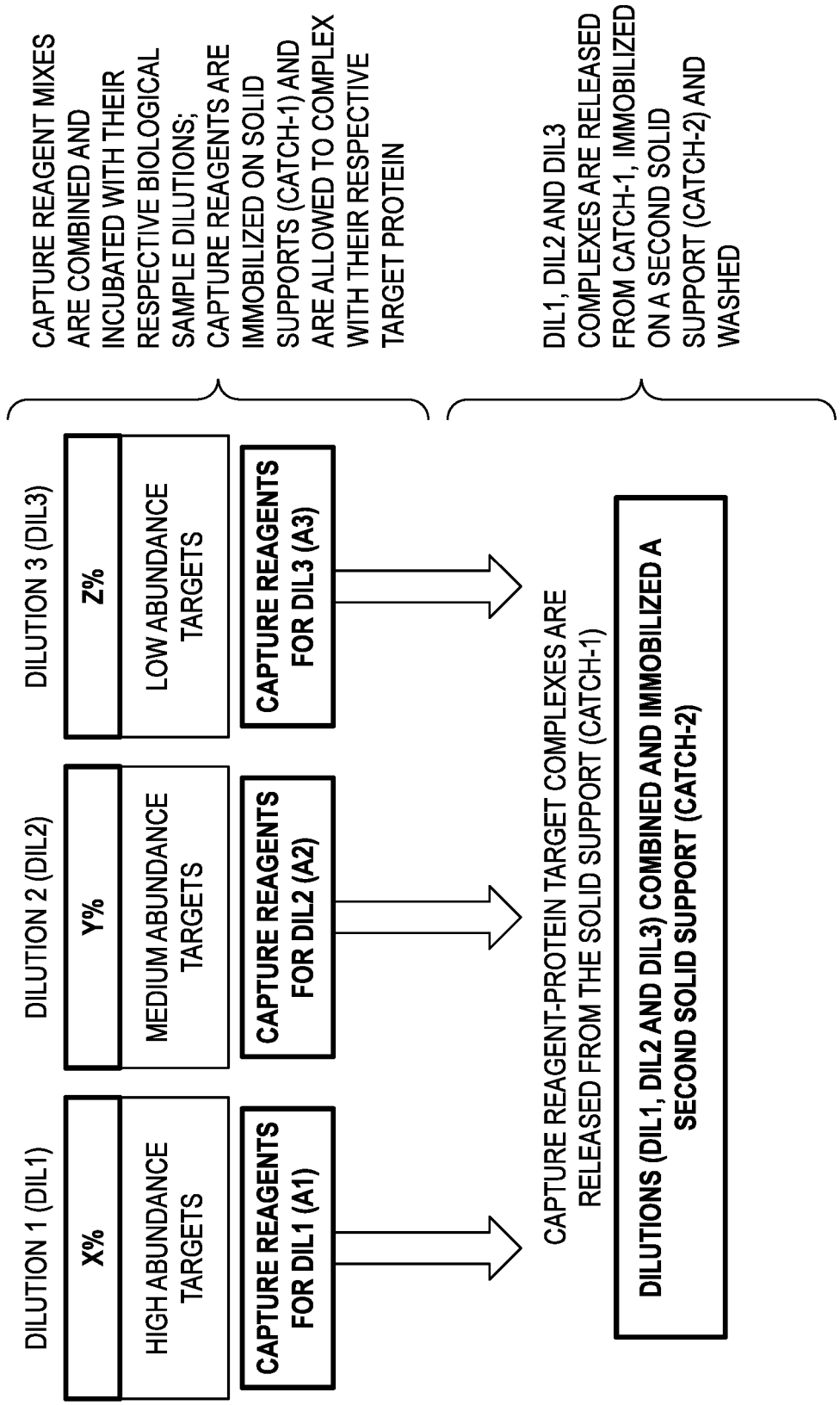
FIG. 10 is a schematic diagram depicting steps of an illustrative method for conducting a two-catch assay, in accordance with aspects of the present teachings.

FIG. 10 provides an example overview of the dilution sets for a biological sample, the corresponding capture reagent sets for their respective dilutions, and the general overview of the two-catch system (catch-1 and catch-2). Three different dilution groups may be created from a biological sample that includes a Z % dilution of the biological sample or DIL3, a Y % dilution of the biological sample or DIL2 and a X % dilution of the biological sample or DIL1, where Z is greater than Y, and Y is greater than X (or Z is a greater dilution than the Y dilution, and the Y dilution is a greater dilution than the X dilution). Each dilution has its own set of corresponding capture reagents (A1 for DIL1, A2 for DIL2 and A3 for DIL3) that bind to a specific set of proteins.

Figure 11:
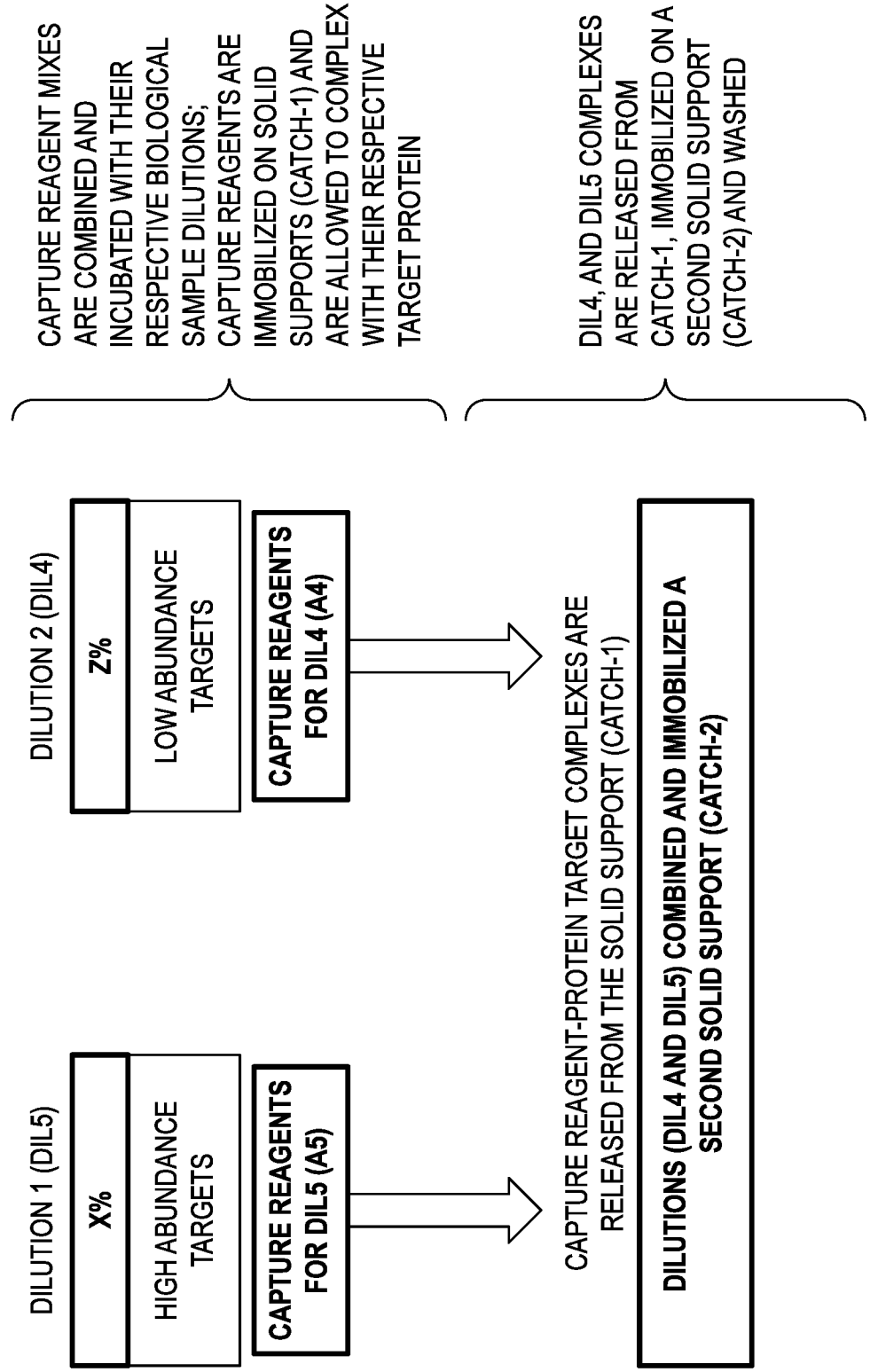
FIG. 11 is a schematic diagram depicting steps of another illustrative method for conducting a two-catch assay, in accordance with aspects of the present teachings.

FIG. 11 provides an example overview of the dilution sets for a biological sample, the corresponding capture reagent sets for their respective dilutions, and the general overview of the two-catch system (catch-1 and catch-2). Two different dilution groups may be created from a biological sample that includes a Z % dilution of the biological sample or DIL4 and an X % dilution of the biological sample or DIL5, where Z is greater than X (or Z is a lesser dilution than the X dilution). Each dilution has its own set of corresponding capture reagents (A4 for DIL4 and A5 for DIL5) that bind to a specific set of proteins.

Figure 12:
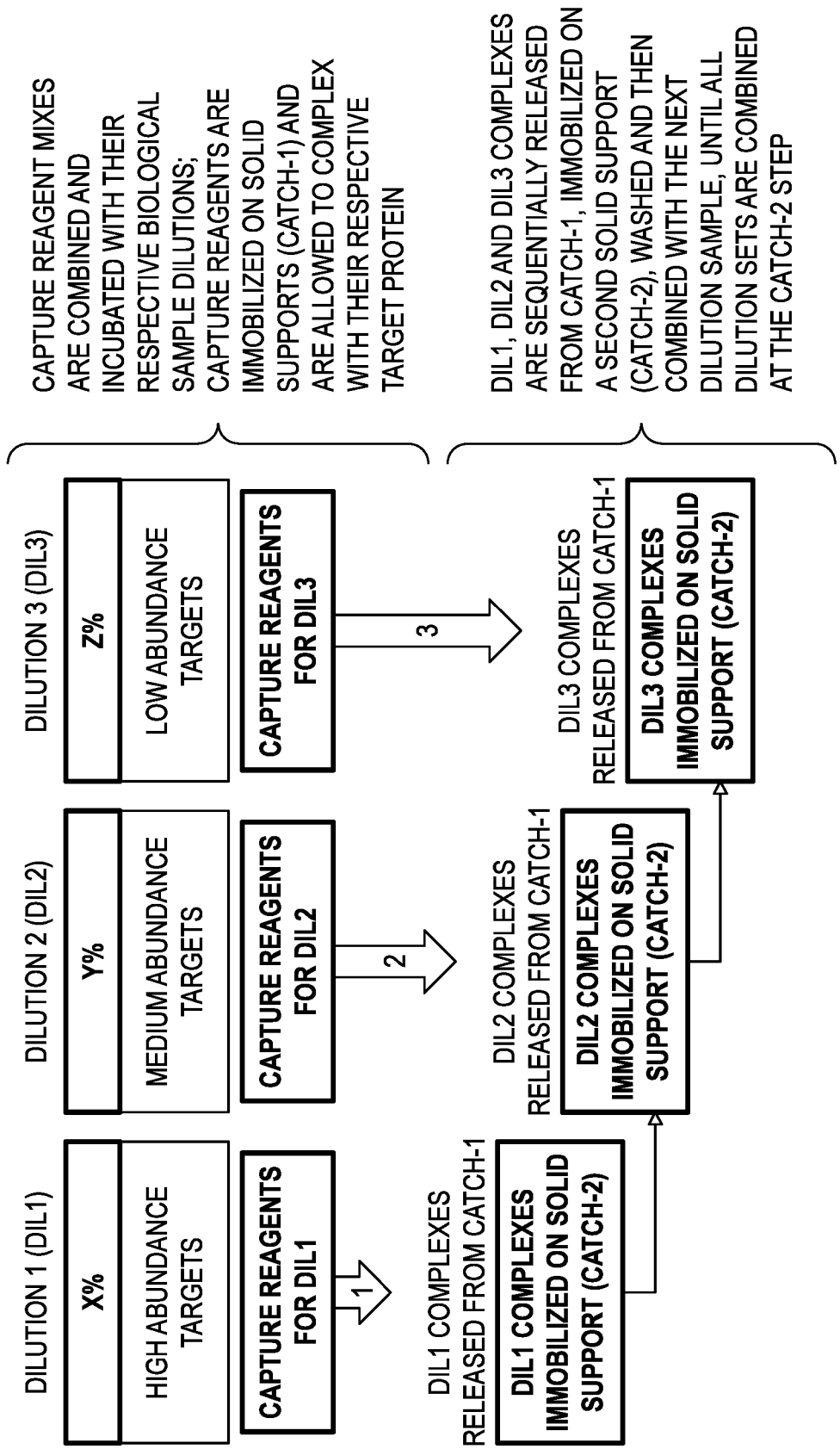
FIG. 12 is a schematic diagram depicting steps of an illustrative sequential two-catch assay method, in accordance with aspects of the present teachings.

FIG. 12 provides an example overview of the dilution sets for a biological sample, the corresponding capture reagent sets for their respective dilutions, and the general overview of the sequential two-catch system (catch-1 and catch-2). Three different dilution groups may be created from a biological sample that includes a Z % dilution of the biological sample or DIL3, a Y % dilution of the biological sample or DIL2 and a X % dilution of the biological sample or DIL1, where Z is greater than Y, and Y is greater than X (or Z is a lesser dilution than the Y dilution, and the Y dilution is a lesser dilution than the X dilution). Each dilution has its own set of corresponding capture reagents (A1 for DIL1, A2 for DIL2 and A3 for DIL3) that bind to a specific set of proteins.

Method 450 is an example of an improved method to perform aptamer- and photoaptamer-based multiplexed assays for the quantification of one or more target molecule(s) that may be present in a test sample wherein the aptamer (or photoaptamer) can be separated from the aptamer-target affinity complex (or photoaptamer-target covalent complex) for final detection using any suitable nucleic acid detection method, wherein detection includes hybridization in an automatically controlled oven in accordance with aspects of the present teachings. Photoaptamers are aptamers that comprise photoreactive functional groups that enable the aptamers to covalently bind or "photocrosslink" their target molecules. The improved aptamer- and photoaptamer-based multiplexed assays described herein can be performed with any suitable aptamers and/or photoaptamers.

Historically, two unanticipated limitations emerged from performing single- and multi-plex aptamer-based assays, including multiplexed proteomic aptamer affinity assays. First, aptamer/aptamer interactions were identified as a primary source of assay background and a potential limitation to multiplex capacity. Second, sample matrices (primarily serum and plasma) were found to inhibit the immobilization of biotinylated aptamers on streptavidin-substituted matrices.

One improvement in the assay, as described in Gold et al. (Gold et al. (December 2010) PLoS One 5(12):e15005), comprised the use of organic solvents in some of the wash buffers of the Catch-2 step to diminish the dielectric constant of the medium. Addition of these wash buffers effectively accented the like-charge repulsion of adjacent phosphodiester backbones of the aptamers, thus promoting dissociation of background-causing interacting aptamers.

Another improvement in the process involves the addition of organic solvents to some of wash buffers used in the Catch-2 step of the assay, it also counters the tendency of aptamers to interact, and thus diminishes background and increases multiplex capacity. However, its primary advantage is to counteract the matrix-dependent inhibition of biotinylated aptamer adsorption to streptavidin matrices. Such inhibition is easily detectable even at 5% v/v plasma or serum, and limits working assay concentrations to 5-10% plasma or serum concentrations. This limitation in turn limits assay sensitivity.

Yet another improvement to the multiplexed assay comprises pre-immobilization of the tagged aptamers on the solid support matrices prior to incubation (termed "Catch-0") with the test solution. Incubation with the test solution is then carried out with bound aptamers, in the processing vessels themselves. As described herein for purposes of illustration only, biotinylated aptamers were pre-immobilized on streptavidin bead matrices, and incubation with test solution carried out with the bead-bound aptamers. This pre-immobilization step enables immobilization under conditions where aptamers have diminished tendency to interact and also enables very stringent washes (with base and with chaotropic salts) prior to incubation, disrupting interacting aptamers and removing all aptamers not bound through the very robust biotin-streptavidin interaction. This reduces the number of aptamer "clumps" traversing the assay—clumps that have at some detectable frequency retained the biotin moiety or become biotinylated in the assay. It is worth noting that irradiation cleaves most, but not all photocleavable biotin moieties from aptamers, while some aptamers become biotinylated via the NHS-biotin treatment intended to "tag" proteins. Biotinylated aptamer that is captured at the Catch-2 step creates background by interacting with bulk photocleaved aptamer, which is then released upon elution. It should also be noted that a pre-immobilized format will likely support very high multiplex capacities as aptamer panels may be immobilized separately then combined in bead-bound form, thus bypassing conditions in which aptamers may interact and clump.

Thus, pre-immobilization bypasses the need for aptamer adsorption in the presence of analyte solution, thus ensuring quantitative immobilization even when assaying inhibitory concentrations of analyte solutions. This enables the use of much higher concentrations, up to and including at least 40% v/v plasma or serum, rather than the 10% top concentration of the process as previously described (Gold et al. (December 2010) PLoS One 5(12):e15005) or the 5% top concentration used in more recent editions of the process thereby increasing sensitivity roughly 4- to 8-fold, as well as, increasing the overall robustness of the assay.

Another improvement to the overall process comprises the use of a chaotropic salt at about a neutral pH for elution during the Catch-2 step as described in detail below. Prior methods comprised the use of sodium chloride at high pH (10), which disrupts DNA hybridization and aptamer/aptamer interaction as well as protein/aptamer interaction. As noted above, DNA hybridization and aptamer/aptamer interactions contribute to assay background. Chaotropic salts, including but not limited to sodium perchlorate, lithium chloride, sodium chloride and magnesium chloride at neutral pH, support DNA hybridization and aptamer/aptamer interactions, while disrupting aptamer/protein interactions. The net result is significantly diminished (about 10-fold) background, with a concomitant rise in assay sensitivity.

As used herein "Catch-1" refers to the partitioning of an aptamer-target affinity complex or aptamer-target covalent complex. The purpose of Catch-1 is to remove substantially all of the components in the test sample that are not associated with the aptamer. Removing the majority of such components will generally improve target tagging efficiency by removing non-target molecules from the target tagging step used for Catch-2 capture and may lead to lower assay background. In one embodiment, a tag is attached to the aptamer either before the assay, during preparation of the assay, or during the assay by appending the tag to the aptamer. In one embodiment, the tag is a releasable tag. In one embodiment, the releasable tag comprises a cleavable linker and a tag. As described above, tagged aptamer can be captured on a solid support where the solid support comprises a capture element appropriate for the tag. The solid support can then be washed as described herein prior to equilibration with the test sample to remove any unwanted materials (Catch-0).

As used herein "Catch-2" refers to the partitioning of an aptamer-target affinity complex or aptamer-target covalent complex based on the capture of the target molecule. The purpose of the Catch-2 step is to remove free, or uncomplexed, aptamer from the test sample prior to detection and optional quantification. Removing free aptamer from the sample allows for the detection of the aptamer-target affinity or aptamer-target covalent complexes by any suitable nucleic acid detection technique. When using Q-PCR for detection and optional quantification, the removal of free aptamer is needed for accurate detection and quantification of the target molecule.

In one embodiment, the target molecule is a protein or peptide and free aptamer is partitioned from the aptamer-target affinity (or covalent) complex (and the rest of the test sample) using reagents that can be incorporated into proteins (and peptides) and complexes that include proteins (or peptides), such as, for example, an aptamer-target affinity (or covalent) complex. The tagged protein (or peptide) and aptamer-target affinity (or covalent) complex can be immobilized on a solid support, enabling partitioning of the protein (or peptide) and the aptamer-target affinity (or covalent) complex from free aptamer. Such tagging can include, for example, a biotin moiety that can be incorporated into the protein or peptide.

In one embodiment, a Catch-2 tag is attached to the protein (or peptide) either before the assay, during preparation of the assay, or during the assay by chemically attaching the tag to the targets. In one embodiment the Catch-2 tag is a releasable tag. In one embodiment, the releasable tag comprises a cleavable linker and a tag. It is generally not necessary, however, to release the protein (or peptide) from the Catch-2 solid support. As described above, tagged targets can be captured on a second solid support where the solid support comprises a capture element appropriate for the target tag. The solid support is then washed with various buffered solutions including buffered solutions comprising organic solvents and buffered solutions comprising salts and/or detergents containing salts and/or detergents.

After washing the second solid support, the aptamer-target affinity complexes are then subject to a dissociation step in which the complexes are disrupted to yield free aptamer while the target molecules generally remain bound to the solid support through the binding interaction of the capture element and target capture tag. The aptamer can be released from the aptamer-target affinity complex by any method that disrupts the structure of either the aptamer or the target. This may be achieved though washing of the support bound aptamer-target affinity complexes in high salt buffer which dissociates the non-covalently bound aptamer-target complexes. Eluted free aptamers are collected and detected.

In another embodiment, high or low pH is used to disrupt the aptamer-target affinity complexes. In another embodiment high temperature is used to dissociate aptamer-target affinity complexes. In another embodiment, a combination of any of the above methods may be used. In another embodiment, proteolytic digestion of the protein moiety of the aptamer-target affinity complex is used to release the aptamer component.

In the case of aptamer-target covalent complexes, release of the aptamer for subsequent quantification is accomplished using a cleavable linker in the aptamer construct. In another embodiment, a cleavable linker in the target tag will result in the release of the aptamer-target covalent complex.

As used herein, a "releasable" or "cleavable" element, moiety, or linker refers to a molecular structure that can be broken to produce two separate components. A releasable (or cleavable) element may comprise a single molecule in which a chemical bond can be broken (referred to herein as an "inline cleavable linker"), or it may comprise two or more molecules in which a non-covalent interaction can be broken or disrupted (referred to herein as a "hybridization linker").

In some embodiments, certain functional groups are spatially separated from others to prevent interference with the individual functionalities. For example, the presence of a label, which absorbs certain wavelengths of light, proximate to a photocleavable group can interfere with the efficiency of photocleavage. It is therefore desirable to separate such groups with a non-interfering moiety that provides sufficient spatial separation to recover full activity of photocleavage, for example. In some embodiments, a "spacing linker" has been introduced into an aptamer with both a label and photocleavage functionality.

"Solid support" refers to any substrate having a surface to which molecules may be attached, directly or indirectly, through either covalent or non-covalent bonds. The solid support may include any substrate material that is capable of providing physical support for the capture elements or probes that are attached to the surface. The material is generally capable of enduring conditions related to the attachment of the capture elements or probes to the surface and any subsequent treatment, handling, or processing encountered during the performance of an assay. The materials may be naturally occurring, synthetic, or a modification of a naturally occurring material. Suitable solid support materials may include silicon, a silicon wafer chip, graphite, mirrored surfaces, laminates, membranes, ceramics, plastics (including polymers such as, e.g., poly(vinyl chloride), cyclo-olefin copolymers, agarose gels or beads, polyacrylamide, polyacrylate, polyethylene, polypropylene, poly(4-methylbutene), polystyrene, polymethacrylate, poly(ethylene terephthalate), polytetrafluoroethylene (PTFE or Teflon®), nylon, poly(vinyl butyrate)), germanium, gallium arsenide, gold, silver, Langmuir Blodgett films, a flow through chip, etc., either used by themselves or in conjunction with other materials. Additional rigid materials may be considered, such as glass, which includes silica and further includes, for example, glass that is available as Bioglass. Other materials that may be employed include porous materials, such as, for example, controlled pore glass beads, crosslinked beaded Sepharose® or agarose resins, or copolymers of crosslinked bis-acrylamide and azalactone. Other beads include nanoparticles, polymer beads, solid core beads, paramagnetic beads, or microbeads. Any other materials known in the art that are capable of having one or more functional groups, such as any of an amino, carboxyl, thiol, or hydroxyl functional group, for example, incorporated on its surface, are also contemplated.

The material used for a solid support may take any of a variety of configurations ranging from simple to complex. The solid support can have any one of a number of shapes, including a strip, plate, disk, rod, particle, bead, tube, well (microtiter), and the like. The solid support may be porous or non-porous, magnetic, paramagnetic, or non-magnetic, polydisperse or monodisperse, hydrophilic or hydrophobic. The solid support may also be in the form of a gel or slurry of closely-packed (as in a column matrix) or loosely-packed particles.

In one embodiment, the solid support with attached capture element is used to capture tagged aptamer-target affinity complexes or aptamer-target covalent complexes from a test mixture. In one particular example, when the tag is a biotin moiety, the solid support could be a streptavidin-coated bead or resin such as Dynabeads M-280 Streptavidin, Dynabeads MyOne Streptavidin, Dynabeads M-270 Streptavidin (Invitrogen), Streptavidin Agarose Resin (Pierce), Streptavidin Ultralink Resin, MagnaBind Streptavidin Beads (ThermoFisher Scientific), BioMag Streptavidin, ProMag Streptavidin, Silica Streptavidin (Bangs Laboratories), Streptavidin Sepharose High Performance (GE Healthcare), Streptavidin Polystyrene Microspheres (Microspheres-Nanospheres), Streptavidin Coated Polystyrene Particles (Spherotech), or any other streptavidin coated bead or resin commonly used by one skilled in the art to capture biotin-tagged molecules.

An advantage of the assay method described herein is that it converts a protein signal into an aptamer signal. As a result, the quantity of aptamers collected/detected is indicative of, and may be directly proportional to, the quantity of target molecules bound and to the quantity of target molecules in the sample. A number of detection schemes can be employed without eluting the aptamer-target affinity or aptamer-target covalent complex from the second solid support after Catch-2 partitioning.

Many detection methods require an explicit label to be incorporated into the aptamer prior to detection. In these embodiments, labels, such as, for example, fluorescent or chemiluminescent dyes can be incorporated into aptamers either during or post synthesis using standard techniques for nucleic acid synthesis. Radioactive labels can be incorporated either during synthesis or post synthesis using standard enzyme reactions with the appropriate reagents. Labeling can also occur after the Catch-2 partitioning and elution by using suitable enzymatic techniques. For example, using a primer with the above-mentioned labels, PCR will incorporate labels into the amplification product of the eluted aptamers. When using a gel technique for quantification, different size mass labels can be incorporated using PCR as well. These mass labels can also incorporate different fluorescent or chemiluminescent dyes for additional multiplexing capacity. Labels may be added indirectly to aptamers by using a specific tag incorporated into the aptamer, either during synthesis or post synthetically, and then adding a probe that associates with the tag and carries the label. The labels include those described above as well as enzymes used in standard assays for colorimetric readouts, for example. These enzymes work in combination with enzyme substrates and include enzymes such as, for example, horseradish peroxidase (HRP) and alkaline phosphatase (AP). Labels may also include materials or compounds that are electrochemical functional groups for electrochemical detection.

For example, the aptamer may be labeled, as described above, with a radioactive isotope such as 32 P prior to contacting the test sample. Employing any one of the four basic assays, and variations thereof as discussed above, aptamer detection may be simply accomplished by quantifying the radioactivity on the second solid support at the end of the assay. The counts of radioactivity will be directly proportional to the amount of target in the original test sample. Similarly, labeling an aptamer with a fluorescent dye, as described above, before contacting the test sample allows for a simple fluorescent readout directly on the second solid support. A chemiluminescent label or a quantum dot can be similarly employed for direct readout from the second solid support, requiring no aptamer elution.

By eluting the aptamer or releasing photoaptamer-target covalent complex from the second solid support additional detection schemes can be employed in addition to those described above. For example, the released aptamer, photoaptamer or photoaptamer-target covalent complex can be run on a PAGE gel and detected and optionally quantified with a nucleic acid stain, such as SYBR Gold. Alternatively, the released aptamer, photoaptamer or photoaptamer covalent complex can be detected and quantified using capillary gel electrophoresis (CGE) using a fluorescent label incorporated in the aptamer as described above. Another detection scheme employs quantitative PCR to detect and quantify the eluted aptamer using SYBR Green, for example. Alternatively, the Invader® DNA assay may be employed to detect and quantify the eluted aptamer. Another alternative detection scheme employs next generation sequencing.

In another embodiment, the amount or concentration of the aptamer-target affinity complex (or aptamer-target covalent complex) is determined using a "molecular beacon" during a replicative process (see, e.g., Tyagi et ah, Nat. Biotech. J_6:49 53, 1998; U.S. Pat. No. 5,925,517). A molecular beacon is a specific nucleic acid probe that folds into a hairpin loop and contains a fluorophore on one end and a quencher on the other end of the hairpin structure such that little or no signal is generated by the fluorophore when the hairpin is formed. The loop sequence is specific for a target polynucleotide sequence and, upon hybridizing to the aptamer sequence the hairpin unfolds and thereby generates a fluorescent signal.

For multiplexed detection of a small number of aptamers still bound to the second solid support, fluorescent dyes with different excitation/emission spectra can be employed to detect and quantify two, or three, or five, or up to ten individual aptamers.

Similarly, different sized quantum dots can be employed for multiplexed readouts. The quantum dots can be introduced after partitioning free aptamer from the second solid support. By using aptamer specific hybridization sequences attached to unique quantum dots multiplexed readings for 2, 3, 5, and up to 10 aptamers can be performed. Labeling different aptamers with different radioactive isotopes that can be individually detected, such as 32 P, 3 H, 113JC, and 3 J5JS, can also be used for limited multiplex readouts.

For multiplexed detection of aptamers released from the Catch-2 second solid support, a single fluorescent dye, incorporated into each aptamer as described above, can be used with a quantification method that allows for the identification of the aptamer sequence along with quantification of the aptamer level. Methods include but are not limited to DNA chip hybridization, micro-bead hybridization, next generation sequencing and CGE analysis.

In some examples, a standard DNA hybridization array, or chip, is used to hybridize each aptamer or photoaptamer to a unique or series of unique probes immobilized on a slide or chip such as Agilent arrays, Illumina BeadChip Arrays, NimbleGen arrays or custom printed arrays. Each unique probe is complementary to a sequence on the aptamer. The complementary sequence may be a unique hybridization tag incorporated in the aptamer, or a portion of the aptamer sequence, or the entire aptamer sequence. The aptamers released from the Catch-2 solid support are added to an appropriate hybridization buffer and processed using, in this example, hybridization methods in accordance with aspects of the present teachings (e.g., including at least one change in rotation direction and/or at least one change in rotation speed during the reaction period). For example, the aptamer solution is incubated for 12 hours with a DNA hybridization array at about 60° C. to ensure stringency of hybridization. The arrays are washed and then scanned in a fluorescent slide scanner, producing an image of the aptamer hybridization intensity on each feature of the array. Image segmentation and quantification is accomplished using image processing software, such as ArrayVision. In one embodiment, multiplexed aptamer assays can be detected using up to 25 aptamers, up to 50 aptamers, up to 100 aptamers, up to 200 aptamers, up to 500 aptamers, up to 1000 aptamers, and up to 10,000 aptamers.

In some examples, addressable micro-beads having unique DNA probes complementary to the aptamers as described above are used for hybridization. The micro-beads may be addressable with unique fluorescent dyes, such as Luminex beads technology, or use bar code labels as in the Illumina VeraCode technology, or laser powered transponders. In one embodiment, the aptamers released from the Catch-2 solid support are added to an appropriate hybridization buffer and processed using standard micro-bead hybridization methods. For example, the aptamer solution is incubated for two hours with a set of micro-beads at about 60° C. to ensure stringency of hybridization. The solutions are then processed on a Luminex instrument which counts the individual bead types and quantifies the aptamer fluorescent signal. In another embodiment, the VeraCode beads are contacted with the aptamer solution and hybridized for two hours at about 60° C. and then deposited on a gridded surface and scanned using a slide scanner for identification and fluorescence quantification. In another embodiment, the transponder micro-beads are incubated with the aptamer sample at about 60° C. and then quantified using an appropriate device for the transponder micro-beads. In one embodiment, multiplex aptamer assays can be detected by hybridization to micro-beads using up to 25 aptamers, up to 50 aptamers, up to 100 aptamers, up to 200 aptamers, and up to 500 aptamers.

The sample containing the eluted aptamers can be processed to incorporate unique mass tags along with fluorescent labels as described above. The mass labeled aptamers are then injected into a CGE instrument, essentially a DNA sequencer, and the aptamers are identified by their unique masses and quantified using fluorescence from the dye incorporated during the labeling reaction. One exemplary example of this technique has been developed by Althea Technologies.

In many of the methods described above, the solution of aptamers can be amplified and optionally tagged before quantification. Standard PCR amplification can be used with the solution of aptamers eluted from the Catch-2 solid support. Such amplification can be used prior to DNA array hybridization, micro-bead hybridization, and CGE readout.

In some examples, the aptamer-target affinity complex (or aptamer-target covalent complex) is detected and/or quantified using Q-PCR. As used herein, "Q-PCR" refers to a PCR reaction performed in such a way and under such controlled conditions that the results of the assay are quantitative, that is, the assay is capable of quantifying the amount or concentration of aptamer present in the test sample.

In some examples, the amount or concentration of the aptamer-target affinity complex (or aptamer-target covalent complex) in the test sample is determined using TaqMan® PCR. This technique generally relies on the 5'-3' exonuclease activity of the oligonucleotide replicating enzyme to generate a signal from a targeted sequence. A TaqMan probe is selected based upon the sequence of the aptamer to be quantified and generally includes a 5'-end fluorophore, such as 6-carboxyfluorescein, for example, and a 3'-end quencher, such as, for example, a 6-carboxytetramethylfluorescein, to generate signal as the aptamer sequence is amplified using polymerase chain reaction (PCR). As the polymerase copies the aptamer sequence, the exonuclease activity frees the fluorophore from the probe, which is annealed downstream from the PCR primers, thereby generating signal. The signal increases as replicative product is produced. The amount of PCR product depends upon both the number of replicative cycles performed as well as the starting concentration of the aptamer.

In some examples, the amount or concentration of an aptamer-target affinity complex (or aptamer-target covalent complex) is determined using an intercalating fluorescent dye during the replicative process. The intercalating dye, such as, for example, SYBR® green, generates a large fluorescent signal in the presence of double-stranded DNA as compared to the fluorescent signal generated in the presence of single-stranded DNA. As the double-stranded DNA product is formed during PCR, the signal produced by the dye increases. The magnitude of the signal produced is dependent upon both the number of PCR cycles and the starting concentration of the aptamer.

In some examples, the aptamer-target affinity complex (or aptamer-target covalent complex) is detected and/or quantified using mass spectrometry. Unique mass tags can be introduced using enzymatic techniques described above. For mass spectroscopy readout, no detection label is required, rather the mass itself is used to both identify and, using techniques commonly used by those skilled in the art, quantified based on the location and area under the mass peaks generated during the mass spectroscopy analysis. An example using mass spectroscopy is the MassARRAY® system developed by Sequenom.

A computer program may be utilized to carry out one or more steps of any of the methods disclosed herein. Another aspect of the present disclosure is a computer program product comprising a computer readable storage medium having a computer program stored thereon which, when loaded into a computer, performs or assists in the performance of any of the methods disclosed herein.

One aspect of the present disclosure is a product of any of the methods disclosed herein, namely, an assay result, which may be evaluated at the site of the testing or it may be shipped to another site for evaluation and communication to an interested party at a remote location, if desired. As used herein, "remote location" refers to a location that is physically different than that at which the results are obtained. Accordingly, the results may be sent to a different room, a different building, a different part of city, a different city, and so forth. The data may be transmitted by any suitable means such as, e.g., facsimile, mail, overnight delivery, e-mail, ftp, voice mail, and the like.

"Communicating" information refers to the transmission of the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data.

An illustrative method 450 (see FIG. 16) is described below. Although various steps of method 450 are described below, the steps need not necessarily all be performed, and in some cases may be performed simultaneously or in a different order than the order described.

At step 452, method 450 includes contacting a first dilution sample with a first aptamer, wherein a first aptamer affinity complex is formed by the interaction of the first aptamer with its target molecule if the target molecule is present in the first dilution sample.

At step 454, method 450 includes contacting a second dilution sample with a second aptamer, wherein a second aptamer affinity complex is formed by the interaction of the second aptamer with its target molecule if the target molecule is present in the second dilution sample. The first dilution and the second dilution are different dilutions of the same test sample.

At step 456, method 450 optionally includes contacting a third dilution sample with a third aptamer, wherein a third aptamer affinity complex is formed by the interaction of the third aptamer with its target molecule if the target molecule is present in the third dilution sample. In some examples, the third dilution sample is a different dilution from the first dilution and the second dilution of the same test sample.

At step 458, method 450 includes incubating the first and second dilution samples separately to allow aptamer affinity complex formation.

At step 460, method 450 optionally includes incubating the third dilution sample. In some examples, the third dilution sample is incubated separately from the first and second dilution samples to allow aptamer affinity complex formation of the third aptamer with its target molecule.

At step 462, method 450 includes transferring the first dilution sample with the first aptamer affinity complex to a first mixture, wherein the first aptamer affinity complex is captured on a solid support in the first mixture.

At step 464, which is performed after step 462, method 450 includes transferring the second dilution sample to the first mixture to form a second mixture, wherein the second aptamer affinity complex of the second dilution is captured on a solid support in the second mixture.

At step 468, method 450 optionally includes transferring the third dilution sample to the second mixture to form a third mixture, wherein the third aptamer affinity complex of the third dilution is captured on a solid support in the third mixture.

At step 470, method 450 includes detecting the presence of and/or determining a level (e.g., an amount) of the first aptamer and second aptamer of the first and second aptamer affinity complexes, and/or detecting the presence and/or amount of one or more first and second aptamer affinity complexes. In examples wherein the third dilution sample is included, step 470 further includes detecting the presence of or determining the level of the third aptamer of the third aptamer affinity complex, or the presence or amount of the third aptamer affinity complex.

Detecting a presence and/or amount in this step includes exposing the second mixture (or third mixture, if step 468 was performed) to a suitable probe molecule (e.g., a plurality of probe molecules attached to a functionalized surface) in one or more reaction chambers disposed within a hybridization oven, and automatically controlling a rotation speed and direction of the reaction chamber (e.g., of a rack holding the reaction chamber) to facilitate mixing of the second or third mixture with the probe molecules. Automatically controlling the rotation speed and direction includes automatically adjusting the rotation speed, the rotation direction, or both, at least once during the reaction period. In some examples, the temperature of the hybridization oven is also automatically controlled, and may be adjusted automatically during the reaction. In some examples, the rotation speed and direction are controlled automatically by an electronic controller in accordance with a protocol stored in a memory device accessible to the electronic controller, and the protocol specifies a rotation speed, direction, and optionally a temperature for each of a plurality of time intervals.

H. Illustrative Combinations and Additional Examples

This section describes additional aspects and features of systems and methods for improved mixing in reaction chambers, presented without limitation as a series of paragraphs, some or all of which may be alphanumerically designated for clarity and efficiency. Each of these paragraphs can be combined with one or more other paragraphs, and/or with disclosure from elsewhere in this application, including materials incorporated by reference, in any suitable manner. Some of the paragraphs below expressly refer to and further limit other paragraphs, providing without limitation examples of some of the suitable combinations.

A0. A device for conducting chemical and biochemical reactions and/or assays within an enclosed reaction chamber, comprising: a substrate having a surface or containing a surface with at least a portion of said surface representing a reaction region wherein the surface is functionalized to enable binding of one or more reactants; a cover which sealingly contacts the substrate, to form an enclosure comprising a sealed reaction chamber; wherein a sample fluid containing a cognate that may react to a surface-bound molecule is introduced into the chamber; and the chamber is moved with at least one change in mixing direction to cause the sample fluid to mix uniformly and maintaining conditions within the chamber for a period of time sufficient to allow reaction between the surface-bound molecule and its cognate to occur.

A1. The device of paragraph A0, wherein "mixing" refers to rotation, nutation, planetary centrifugal mixing, and/or other directional mixing methodology.

A2. The device of any one of paragraphs A0-A1, wherein an air bubble is present within the reaction chamber.

A3. The device of any one of paragraphs A0-A2, wherein beads, colloids, and/or other particles are present within the reaction chamber.

A4. The device of any one of paragraphs A0-A3, wherein the maintained reaction conditions (e.g., temperature and/or dilution) within the chamber are altered at least once during each reaction period.

B0. A device for conducting chemical and biochemical reactions and/or assays within an enclosed reaction chamber, comprising: a substrate having a surface or containing a surface with at least a portion of said surface representing a reaction region wherein the surface is functionalized to enable binding of one or more reactants; a cover which sealingly contacts the substrate, to form an enclosure comprising a sealed reaction chamber; wherein a sample fluid containing a cognate that may react to a surface-bound molecule is introduced into the chamber; and the chamber is moved with at least one change in mixing speed to cause the sample fluid to mix uniformly and maintaining conditions within the chamber for a period of time sufficient to allow reaction between the surface-bound molecule and its cognate to occur.

B1. The device of paragraph B0, wherein "mixing" refers to rotation, nutation, and/or other directional mixing methodology.

B2. The device of any one of paragraphs B0-B1, wherein an air bubble is present within the reaction chamber.

B3. The device of any one of paragraphs B0-B2, wherein beads, colloids, and/or other particles are present within the reaction chamber.

B4. The device of any one of paragraphs B0-B3, wherein the maintained reaction conditions within the chamber (e.g., temperature and/or dilution) are altered at least once during reaction period.

C0. A system for facilitating chemical reactions in a reaction chamber with reduced nonuniformity, the system comprising: a rack configured to receive a device including a reaction chamber; a motor configured to rotate the rack; a control unit configured to receive data corresponding to a rotation protocol of the rack; and a motor controller coupled to the control unit and configured to drive the motor to rotate the rack according to the rotation protocol; wherein rotating the rack according to the rotation protocol includes adjusting a characteristic of the rotation at least once during a reaction period.

C1. The system of paragraph C0, wherein the characteristic is a rotation speed.

C1a. The system of paragraph C1, wherein rotating the rack according to the rotation protocol further includes adjusting a direction of the rotation at least once during the reaction period.

C2. The system of paragraph C0, wherein the characteristic is a rotation direction.

C3. The system of any one of paragraphs C0 through C2, further comprising an oven compartment containing the rack; and a temperature controller configured to control a temperature of the oven compartment; wherein the rotation protocol further includes an oven setpoint temperature; and wherein the control unit is coupled to the temperature controller and configured to control the temperature controller to control the oven temperature to the oven setpoint temperature.

C4. The system of paragraph C3, wherein the control unit is configured to adjust the oven setpoint temperature at least once during the reaction period.

C5. The system of any one of paragraphs C0-C4, wherein the rack is configured to hold the device such that an axis orthogonal to a functionalized surface of the reaction chamber is parallel to the rotation axis of the rack.

C6. The system of any one of paragraphs C0-C5, wherein the reaction chamber contains a bubble.

D0. An electronic controller configured to be coupled to a motor controller of a drive motor configured to rotate a hybridization oven rack, wherein the electronic controller is configured to receive a protocol for rotating the rack and to control the motor controller to control the drive motor to rotate the rack in accordance with the protocol, and wherein the protocol includes varying the direction of rotation or the speed of rotation at least once during a predetermined period of time.

E0. A hybridization oven having a motor controller coupled to and controlled by the electronic controller of paragraph D0.

F0. A method comprising: a) contacting a first dilution sample with a first aptamer, wherein a first aptamer affinity complex is formed by the interaction of the first aptamer with its target molecule if the target molecule is present in the first dilution sample; b) contacting a second dilution sample with a second aptamer, wherein a second aptamer affinity complex is formed by the interaction of the second aptamer with its target molecule if the target molecule is present in the second dilution sample; c) incubating the first and second dilution samples separately to allow aptamer affinity complex formation; d) transferring the first dilution sample with the first aptamer affinity complex to a first mixture, wherein the first aptamer affinity complex is captured on a solid support in the first mixture; e) after step d), transferring the second dilution sample to the first mixture to form a second mixture, wherein the second aptamer affinity complex of the second dilution is captured on a solid support in the second mixture; f) detecting for the presence of or determining the level of the first aptamer and second aptamer of the first and second aptamer affinity complexes, or the presence or amount of one or more first and second aptamer affinity complexes; wherein, the first dilution and the second dilution are different dilutions of the same test sample, and wherein step f) includes exposing the second mixture to a suitable probe molecule (e.g., a plurality of probe molecules attached to a functionalized surface) in one or more reaction chambers and mixing the one or more reaction chambers by rotating the one or more reaction chambers within a hybridization oven, and wherein rotating the one or more reaction chambers includes automatically adjusting a speed and/or direction of rotation of the one or more reaction chambers at least once.

F1. The method of paragraph F0, wherein the test sample is selected from plasma, serum, urine, whole blood, leukocytes, peripheral blood mononuclear cells, buffy coat, sputum, tears, mucus, nasal washes, nasal aspirate, semen, saliva, peritoneal washings, ascites, cystic fluid, meningeal fluid, amniotic fluid, glandular fluid, lymph fluid, nipple aspirate, bronchial aspirate, bronchial brushing, synovial fluid, joint aspirate, organ secretions, cells, a cellular extract, and cerebrospinal fluid.

F2. The method of any one of paragraphs F0 through F1, wherein the first and second aptamer-target molecule affinity complexes are non-covalent complexes.

F3. The method of any one of paragraphs F0 through F2, wherein the target molecule is selected from a protein, a peptide, a carbohydrate, a polysaccharide, a glycoprotein, a hormone, a receptor, an antigen, an antibody, a virus, a bacteria, a metabolite, a cofactor, an inhibitor, a drug, a dye, a nutrient, a growth factor, a cell and a tissue.

F4. The method of any one of paragraphs F0 through F3, wherein the first dilution is a dilution of the test sample of from 0.001% to 0.009% (or is 0.001%, 0.002%, 0.003%, 0.004%, 0.005%, 0.006%, 0.007%, 0.008% or 0.009%) or is from 0.002% to 0.008% or is from 0.003% to 0.007% or is about 0.005%, and the second dilution is a dilution of the test sample of from 0.01% to 1% (or is 0.01%, 0.02%, 0.03%, 0.04%, 0.05%, 0.06%, 0.07%, 0.08%, 0.09%, 0.1%, 0.15%, 0.2%, 0.25%, 0.3%, 0.35%, 0.4%, 0.45%, 0.5%, 0.6%, 0.7%, 0.8%, 0.9% or 1%) or is from 0.1% to 0.8% or is from 0.2% to 0.75% or is about 0.5%.

F5. The method of any one of paragraphs F0 through F3, wherein the first dilution is a dilution of the test sample of from 0.001% to 0.009% (or 0.001%, 0.002%, 0.003%, 0.004%, 0.005%, 0.006%, 0.007%, 0.008% or 0.009%) or is from 0.002% to 0.008%, or is from 0.003% to 0.007% or is about 0.005%; and the second dilution is a dilution of the test sample of from 5% to 39% (or is 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38% or 39%), or is from 15% to 30%, or is from 15% to 25%, or is about 20%.

F6. The method of any one of paragraphs F0 through F3, wherein the first dilution is a dilution of the test sample of from 0.01% to 1% (or is 0.01%, 0.02%, 0.03%, 0.04%, 0.05%, 0.06%, 0.07%, 0.08%, 0.09%, 0.1%, 0.15%, 0.2%, 0.25%, 0.3, 0.35%, 0.4%, 0.45%, 0.5%, 0.6%, 0.7%, 0.8%, 0.9% or 1%) or is from 0.1% to 0.8%, or is from 0.2% to 0.75%, or is about 0.5%; and the second dilution is a dilution of the test sample of from 5% to 39% (or is 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38% or 39%), or is from 15% to 30%, or is from 15% to 25%, or is about 20%.

F7. The method of any one of paragraphs F0 through F3, wherein the first dilution is a dilution of the test sample of from 0.01% to 1% (or is 0.01%, 0.02%, 0.03%, 0.04%, 0.05%, 0.06%, 0.07%, 0.08%, 0.09%, 0.1%, 0.15%, 0.2%, 0.25%, 0.3, 0.35%, 0.4%, 0.45%, 0.5%, 0.6%, 0.7%, 0.8%, 0.9% or 1%) or is from 0.1% to 0.8%, or is from 0.2% to 0.75%, or is about 0.5%; and the second dilution is a dilution of the test sample of from 0.001% to 0.009% (or is 0.001%, 0.002%, 0.003%, 0.004%, 0.005%, 0.006%, 0.007%, 0.008% or 0.009%) or is from 0.002% to 0.008%, or is from 0.003% to 0.007%, or is about 0.005%.

F8. The method of any one of paragraphs F0 through F3, wherein the first dilution is a dilution of the test sample of from 5% to 39% (or is 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38% or 39%), or is from 15% to 30%, or is from 15% to 25%, or is about 20%, and the second dilution is a dilution of the test sample of from 0.01% to 1% (or is 0.01%, 0.02%, 0.03%, 0.04%, 0.05%, 0.06%, 0.07%, 0.08%, 0.09%, 0.1%, 0.15%, 0.2%, 0.25%, 0.3, 0.35%, 0.4%, 0.45%, 0.5%, 0.6%, 0.7%, 0.8%, 0.9% or 1%) or is from 0.1% to 0.8%, or is from 0.2% to 0.75%, or is about 0.5%.

F9. The method of claim any one of paragraphs F0 through F3, wherein the first dilution is a dilution of the test sample of from 5% to 39% (or is 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38% or 39%), or is from 15% to 30%, or is from 15% to 25%, or is about 20%, and the second dilution is a dilution of the test sample of from 0.001% to 0.009% (or is 0.001%, 0.002%, 0.003%, 0.004%, 0.005%, 0.006%, 0.007%, 0.008% or 0.009%) or is from 0.002% to 0.008%, or is from 0.003% to 0.007%, or is about 0.005%.

F10. The method of any one of paragraphs F0 through F9, wherein the first aptamer and/or the second aptamer, independently, comprises at least one 5-position modified pyrimidine.

F11. The method of paragraph F10, wherein the at least one 5-position modified pyrimidine comprises a linker at the 5-position of the pyrimidine and a moiety attached to the linker.

F12. The method of paragraph F11, wherein the linker is selected from amide linker, a carbonyl linker, a propynyl linker, an alkyne linker, an ester linker, a urea linker, a carbamate linker, a guanidine linker, an amidine linker, a sulfoxide linker, and a sulfone linker.

F13. The method of paragraph F11, wherein the moiety is a hydrophobic moiety.

F15. The method of paragraph F13, wherein the moiety is selected from a naphthyl moiety, a benzyl moiety, a fluorobenzyl moiety, a tyrosyl moiety, an indole moiety a morpholino moiety, an isobutyl moiety, a 3,4-methylenedioxy benzyl moiety, a benzothiophenyl moiety, and a benzofuranyl moiety.

F16. The method of paragraph F10, wherein the pyrimidine of the 5-position modified pyrimidine is a uridine, cytidine or thymidine.

F17. The method of claim 1, further comprising contacting a third dilution sample with a third aptamer, wherein a third aptamer affinity complex is formed by the interaction of the third aptamer with its target molecule if the target molecule is present in the third dilution sample;

F18. The method of paragraph F17, wherein the third dilution sample is incubated separately from the first and second dilution samples to allow aptamer affinity complex formation of the third aptamer with its target molecule.

F19. The method of paragraph F18, further comprising transferring the third dilution sample to the second mixture to form a third mixture, wherein the third aptamer affinity complex of the third dilution is captured on a solid support in the third mixture.

F20. The method of paragraph F19, further comprising detecting for the presence of or determining the level of the third aptamer of the third aptamer affinity complex, or the presence or amount of the third aptamer affinity complex;

F21. The method of paragraph F17, wherein the third dilution is a different dilution from the first dilution and the second dilution of the same test sample.

F22. The method of paragraph F17, wherein the third dilution is a dilution of the test sample selected from 5% to 39% (or is 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38% or 39%), from 15% to 30%, from 15% to 25%, about 20%; from 0.01% to 1% (or 0.01%, 0.02%, 0.03%, 0.04%, 0.05%, 0.06%, 0.07%, 0.08%, 0.09%, 0.1%, 0.15%, 0.2%, 0.25%, 0.3%, 0.35%, 0.4%, 0.45%, 0.5%, 0.6%, 0.7%, 0.8%, 0.9% or 1%), from 0.1% to 0.8%, from 0.2% to 0.75%, about 0.5%; and from 0.001% to 0.009% (or 0.001%, 0.002%, 0.003%, 0.004%, 0.005%, 0.006%, 0.007%, 0.008% or 0.009%), or from 0.002% to 0.008%, from 0.003% to 0.007%, about 0.005%.

F23. The method of paragraph F17, wherein the third aptamer comprises at least one 5-position modified pyrimidine.

F24. The method of paragraph F23, wherein the at least one 5-positon modified pyrimidine comprises a linker at the 5-position of the pyrimidine and a moiety attached to the linker.

F25. The method of paragraph F24, wherein the linker is selected from amide linker, a carbonyl linker, a propynyl linker, an alkyne linker, an ester linker, a urea linker, a carbamate linker, a guanidine linker, an amidine linker, a sulfoxide linker, and a sulfone linker.

F26. The method of paragraph F24, wherein the moiety is a hydrophobic moiety.

F28. The method of paragraph F26, wherein the moiety is selected from a naphthyl moiety, a benzyl moiety, a fluorobenzyl moiety, a tyrosyl moiety, an indole moiety a morpholino moiety, an isobutyl moiety, a 3,4-methylenedioxy benzyl moiety, a benzothiophenyl moiety, and a benzofuranyl moiety.

F29. The method of paragraph F23, wherein the pyrimidine of the 5-position modified pyrimidine is a uridine, cytidine or thymidine.

G1. A system for facilitating reactions with improved uniformity, the system comprising: a controller configured to control a motor to impart rotational motion to a rotatable rack for a period of time, wherein the rotatable rack is disposed within a reaction oven and is configured to hold at least one reaction chamber, the reaction chamber containing a functionalized surface and a fluid; wherein the controller is configured to control the motor to change a characteristic of the rotational motion at least once during the period of time.

G2. The system of paragraph G1, wherein the characteristic of the rotational motion is a rotational speed of the rotatable rack, and wherein controlling the motor to change the characteristic includes changing the rotational speed from a first nonzero value to a second nonzero value.

G3. The system of paragraph G2, wherein the controller is further configured to control the motor to change a direction of rotation of the rotatable rack at least once during the period of time.

G4. The system of paragraph G1, wherein the controller is configured to control the motor to change the characteristic at an end of a first time interval and at an end of a second time interval, the first time interval and the second time interval occurring within the period of time.

G5. The system of paragraph G1, wherein the controller includes: a motor controller configured to control the motor, and a processor configured to receive instructions for controlling the motor and to control the motor, via the motor controller, based on the received instructions.

G6. The system of paragraph G5, wherein the instructions include instructions for controlling a heating element of the reaction oven, and wherein the processor is further configured to control the heating element based on the received instructions.

G7. The system of paragraph G6, wherein the controller further includes a temperature controller, and the processor is configured to control the heating element via the temperature controller.

G8. The system of paragraph G1, wherein the period of time is at least fifteen hours.

G9. A method for mixing a reaction chamber including a rotatable rack, the method comprising: automatically controlling a motor coupled to the rack to rotate the rack for a first time interval such that the rotation of the rack has a characteristic having a first value; and automatically controlling the motor to rotate the rack for a second time interval such that the characteristic of the rotation has a second value different from the first value.

G9a. The method of paragraph G9, wherein at least one of the first value and the second value is determined randomly.

G10. The method of paragraph G9, wherein the characteristic is a rotational speed of the rack.

G11. The method of paragraph G9, wherein the characteristic is a rotational direction of the rack, and the first and second values are opposite rotational directions.

G12. The method of paragraph G9, wherein the second time interval immediately follows the first time interval.

G13. The method of paragraph G9, wherein the rack is disposed within a hybridization oven, the method further comprising automatically controlling a temperature of the hybridization oven to have a first temperature value during the first time interval and a second temperature value during the second time interval.

G14. The method of paragraph G9, further comprising receiving, at an electronic controller coupled to the motor, instructions executable at the electronic controller to cause the motor to rotate the rack such that the characteristic has the first value during the first time interval and the second value during the second time interval.

G15. The method of paragraph G14, wherein the instructions corresponding to the first time interval and the instructions corresponding to the second time interval are received at the electronic controller prior to a beginning of the first time interval.

G16. A hybridization oven comprising one or more walls defining an oven interior; a rack disposed within the oven interior and configured to hold a vessel including one or more reaction chambers; a drive motor configured to rotate the rack about a rotation axis; and an electronic controller configured to automatically control the drive motor to rotate the rack for a duration of time and to automatically adjust a characteristic of the rotation of the rack at least once during the duration.

G17. The hybridization oven of paragraph G16, wherein the characteristic of the rotation is a speed of rotation of the rack.

G18. The hybridization oven of paragraph G17, wherein the electronic controller is further configured to automatically adjust a direction of rotation of the rack at least once during the duration.

G19. The hybridization oven of paragraph G18, further comprising a heating element, wherein the electronic controller is configured to automatically control the heating element to control a temperature of the oven and to automatically adjust the temperature of the oven at least once during the duration.

G20. The hybridization oven of paragraph G19, wherein the electronic controller comprises a temperature controller configured to automatically control the heating element, a motor controller configured to automatically control the drive motor, and a processor configured to control the temperature controller and the motor controller.

CONCLUSION

The disclosure set forth above may encompass multiple distinct examples with independent utility. Although each of these has been disclosed in its preferred form(s), the specific embodiments thereof as disclosed and illustrated herein are not to be considered in a limiting sense, because numerous variations are possible. Certain combinations and subcombinations regarded as novel and nonobvious are particularly pointed out throughout this disclosure. Other combinations and subcombinations of features, functions, elements, and/or properties may be claimed, with or without variation in scope, in applications claiming priority from this or a related application.

Explicit reference is hereby made to all examples, embodiments, inventions, labels, terms, descriptions, and illustrative measurements shown in the drawings and/or in any included appendices, whether or not described further herein. To the extent that section headings are used within this disclosure, such headings are for organizational purposes only.

The invention claimed is:
1. A system for facilitating reactions, comprising:
 a reaction oven;
 at least one reaction chamber, the at least one reaction chamber containing a functionalized surface and a fluid;

a rotatable rack disposed within the reaction oven, the rotatable rack configured to hold the at least one reaction chamber;

a motor; and a controller configured to control the motor to impart rotational motion to the rotatable rack for a period of time and to control a heating element to adjust a temperature of the reaction oven;

wherein the controller is configured to control the motor to change a characteristic of the rotational motion and to control the heating element to adjust the temperature of the reaction oven at least once during the period of time according to a protocol stored in a memory accessible by the controller, wherein the protocol defines a plurality of time intervals, a respective value of the characteristic of the rotational motion for each of the time intervals, and a respective temperature for each of the time intervals, and wherein the values of the characteristic of the rotational motion are randomly selected from a first distribution and the temperatures are randomly selected from a second distribution.

2. The system of claim 1, wherein the characteristic of the rotational motion is a rotational speed of the rotatable rack.

3. The system of claim 2, wherein the controller is further configured to control the motor to change a direction of rotation of the rotatable rack at least once during the period of time.

4. The system of claim 1, wherein the controller is configured to control the motor to change the characteristic of the rotational motion at an end of a first time interval and at an end of a second time interval, the first time interval and the second time interval occurring within the period of time.

5. The system of claim 1, wherein the controller is configured to control the motor by controlling a motor controller coupled to the motor and is configured to control the heating element by controlling a temperature controller coupled to the heating element.

6. The system of claim 1, wherein the characteristic of the rotational motion is a vector of angular velocity comprising a direction of rotation of the rack, a speed of rotation of the rack, and an axis of rotation of the rack.

7. A method for mixing a reaction chamber attached to a rotatable rack, the method comprising:

automatically controlling a motor coupled to the rack to rotate the rack for a first time interval such that the rotation of the rack has a characteristic having a first value;

automatically controlling the motor to rotate the rack for a second time interval such that the characteristic of the rotation has a second value different from the first value;

automatically controlling a heating element in the reaction chamber to heat the reaction chamber for a third time interval to a characteristic first temperature; and automatically controlling the heating element to heat the reaction chamber for a fourth time interval to a characteristic second temperature different from the first temperature;

wherein the values of the characteristic of the rotation are randomly selected from a first distribution and the temperatures are randomly selected from a second distribution.

8. The method of claim 7, wherein the characteristic of the rotation is a rotational speed of the rack.

9. The method of claim 7, wherein the characteristic of the rotation is a rotational direction of the rack, and the first and second values of the characteristic of the rotation are opposite rotational directions.

10. The method of claim 7, wherein the second time interval immediately follows the first time interval.

11. The method of claim 7, further comprising receiving, at an electronic controller coupled to the motor, instructions executable at the electronic controller to cause the motor to rotate the rack such that the characteristic of the rotation has the first value during the first time interval and the second value during the second time interval.

12. The method of claim 11, wherein the instructions corresponding to the first time interval and the instructions corresponding to the second time interval are received at the electronic controller prior to a beginning of the first time interval.

13. A hybridization oven comprising:

one or more walls defining an oven interior;

a rack disposed within the oven interior and configured to hold a vessel including one or more reaction chambers;

a drive motor configured to rotate the rack about a rotation axis;

a heating element configured to heat the oven interior to a desired temperature; and an electronic controller configured to automatically control the drive motor to rotate the rack for a duration of time and to automatically adjust a characteristic of the rotation of the rack at least once during the duration and to control the heating element to automatically adjust the temperature of the reaction oven at least once during the duration according to a protocol stored in a memory accessible by the controller, wherein the protocol defines a plurality of time intervals, a respective value of the characteristic of the rotation for each of the time intervals, and a respective temperature for each of the time intervals, and wherein the values of the characteristic of the rotation are randomly selected from a first distribution and the temperatures are randomly selected from a second distribution.

14. The hybridization oven of claim 13, wherein the characteristic of the rotation is a speed of rotation of the rack.

15. The hybridization oven of claim 14, wherein the electronic controller is further configured to automatically adjust a direction of rotation of the rack at least once during the duration.

16. The hybridization oven of claim 13, wherein the electronic controller comprises a temperature controller configured to automatically control the heating element, a motor controller configured to automatically control the drive motor, and a processor configured to control the temperature controller and the motor controller.

17. The hybridization oven of claim 13, wherein the values of the characteristic of the rotation are values of torque applied by the motor to the rack.

18. The hybridization oven of claim 13, wherein the values of the characteristic of the rotation are values of electric current provided to the motor.

19. The hybridization oven of claim 13, wherein the characteristic of the rotation is a direction of rotation of the rack.

* * * * *